United States Patent
Zhu et al.

(10) Patent No.: US 10,899,781 B2
(45) Date of Patent: Jan. 26, 2021

(54) PLATINUM COMPLEX, ITS PREPARATION AND THERAPEUTIC USE

(71) Applicant: City University of Hong Kong, Kowloon (HK)

(72) Inventors: Guangyu Zhu, Mid-level West (HK); Zhigang Wang, Kowloon (HK); Zoufeng Xu, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/917,966

(22) Filed: Mar. 12, 2018

(65) Prior Publication Data

US 2019/0276486 A1    Sep. 12, 2019

(51) Int. Cl.
| | | |
|---|---|---|
| *C07F 15/00* | (2006.01) | |
| *A61P 35/00* | (2006.01) | |
| *A61N 5/06* | (2006.01) | |
| *A61K 41/00* | (2020.01) | |

(52) U.S. Cl.
CPC ...... *C07F 15/0093* (2013.01); *A61K 41/0057* (2013.01); *A61N 5/062* (2013.01); *A61P 35/00* (2018.01); *A61N 2005/0662* (2013.01)

(58) Field of Classification Search
None
See application file for complete search history.

(56) References Cited

U.S. PATENT DOCUMENTS

2013/0210756 A1*  8/2013  Kim .................. A61K 41/0071
                                                    514/34

OTHER PUBLICATIONS

STN Registry entry, RN 118015-59-1 entered into the database on Dec. 16, 1988. (Year: 1988).*

* cited by examiner

*Primary Examiner* — Jeffrey S Lundgren
*Assistant Examiner* — Michael J Schmitt
(74) *Attorney, Agent, or Firm* — Renner Kenner Greive Bobak Taylor & Weber

(57) ABSTRACT

A platinum complex includes a structure of Formula (I). A method for treating a subject suffering from cancer includes a step of administering an effective amount of the platinum complex to the subject. A method for inhibiting the growth of cancer cells includes the step of contacting a population of cancer cells with an effective amount of the platinum complex. The platinum complexes are particularly suitable for treatment of cancer through, in particular, photodynamic therapy.

34 Claims, 8 Drawing Sheets

PLATINUM COMPLEX, ITS PREPARATION AND THERAPEUTIC USE

TECHNICAL FIELD

The present application relates to a novel platinum complex in particularly but not exclusively to a photo-activatable platinum complex. The present invention also relates to the preparation of the platinum complex as well as the use of it in treating a disease in particular but not exclusively a cancer.

BACKGROUND OF THE INVENTION

Cancer remains a life-threatening disease affecting a steadily increasing number of people overall in the world. Platinum-based chemotherapeutic compounds, including cisplatin, carboplatin and oxaliplatin, have been widely applied for the treatment of different types of cancer in clinical trials for decades. Despite their prominent therapeutic effects, severe side effects such as nephrotoxicity, neurotoxicity, nausea, vomiting, and hair loss limit the clinical application of these compounds. The side effects are found to be caused by the non-specific activation of the compounds, followed by non-specific binding to biomolecules rather than genomic DNA.

Platinum(IV)-based prodrugs have been reported to be used to control the activation of the platinum-based chemotherapeutic compounds. These prodrugs may be activated through reduction to their platinum(II) equivalents by cellular reductants such as ascorbate, glutathione, and other cytosine-containing molecules. However, this type of prodrugs may be activated in normal organs due to the ubiquitous existence in body. An alternative way is to use light to control the activation process of platinum(IV) prodrug. Current photo-activatable platinum (IV) prodrugs have limited biomedical application as most of them can only be activated by light in the region of ultraviolet or blue light which has poor tissue penetration.

Thus, there remains a strong need for new and effective compounds suitable for treating cancer with acceptable side effects that can be used either as alternatives or alternatively in addition to common chemotherapeutic compounds such as cisplatin or other anticancer therapies such as radiotherapy and which are effective even if the cancer is or has developed chemoresistance against commonly used chemotherapeutic compounds such as cisplatin.

SUMMARY OF THE INVENTION

The first aspect of the present invention provides a platinum complex comprising a structure of Formula (I):

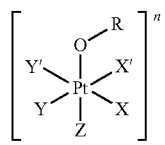

wherein:
X, X', Y, Y' and Z are independently selected from an electron donor ligand, optionally X and X' are linked to form a first bidentate ligand, and Y and Y' are linked to form a second bidentate ligand;

n is selected from zero, any positive charge or any negative charge;
R is a fluorophore moiety having a structure of Formula (II) or Formula

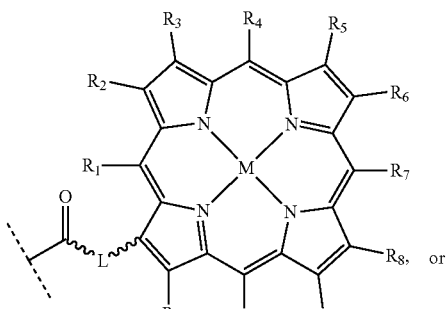

Formula (II)

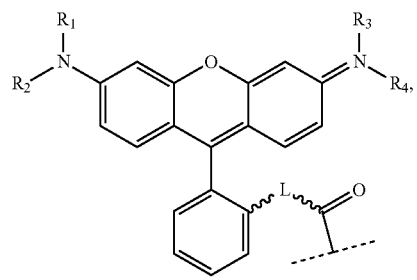

Formula (III)

and
with M being $H_2$ or a metal atom, L being a linker group, and $R_1$ to $R_{11}$ each being independently a substituent or a hydrogen atom, wherein an adjacent pair of $R_1$ to $R_{11}$ may form a fused heterocyclic or carbocyclic ring.

The second aspect of the present invention pertains to a method of preparing the platinum complex described above, i.e. for preparing a platinum complex comprising a structure of Formula (I):

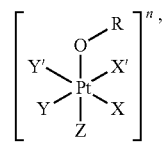

Formula (I)

with X, X', Y, Y' and Z, n and R as described above.

The present invention further provides a pharmaceutical composition comprising:
(i) a platinum complex as described above; and
(ii) a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof.

According to the invention is also the platinum complex described above for use as a medicament for the treatment of cancer. The platinum complex can be used in an effective amount for treating a living organism like an animal or a human, in particular a mammal, preferably a human. Another aspect of the invention refers to the use of the platinum complex described above in the preparation of a medicament for treatment of cancer.

The platinum complex described above may be used in photodynamic therapy or targeted therapy.

In a further aspect, the invention provides a method for inhibiting the growth of cancer cells. The method comprises the step of contacting a population of cancer cells with the platinum complex as described above. In particular, the cell growth is reduced and/or cell death is induced.

Those skilled in the art will appreciate that the invention described herein is susceptible to variations and modifications other than those specifically described.

The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1A:
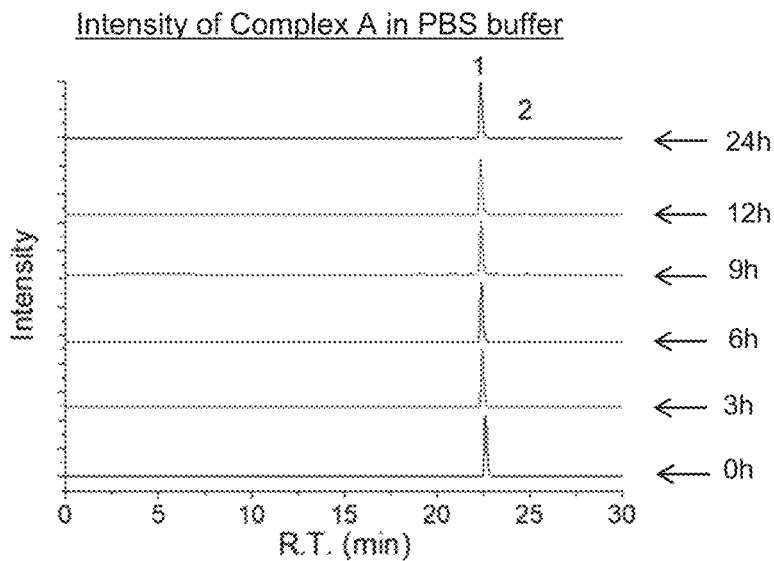
FIG. 1a is a plot showing the intensity of Complex A prepared in an embodiment of the present invention in phosphate buffered saline (pH7.4) in dark at various time slots (0 h, 3 h, 6 h, 9 h, 12 h, and 24 h), measured by RP-HPLC. Peak 1 corresponds to the intensity of Complex A, and Peak 2 corresponds to the intensity of pyropheophorbide a (PPA).

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise. Other than in the working examples, or where otherwise indicated, all numbers used herein should be understood as modified in all instances by the term "about" The term "about" when used in connection with a number can mean, for example, ±2%.

Moreover, the words "example" or "exemplary" used in this invention are intended to serve as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

The present invention provides a platinum complex, in particular a photo-activatable platinum complex, comprising a structure of Formula (I):

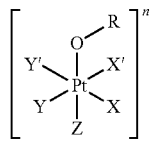

wherein:
X, X', Y, Y' and Z are independently selected from an electron donor ligand, optionally X and X' are linked to form a first bidentate ligand, and Y and Y' are linked to form a second bidentate ligand;
n is selected from zero, any positive charge or any negative charge;
R is a fluorophore moiety having a structure of Formula (II) or Formula (III):

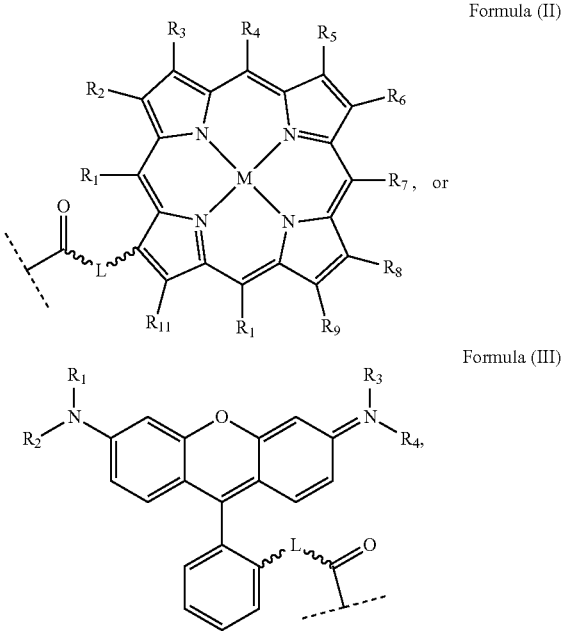

and
with M being $H_2$ or a metal atom, L being a linker group, and $R_1$ to $R_{11}$ each being independently a substituent or a hydrogen atom, wherein an adjacent pair of $R_1$ to $R_{11}$ may form a fused heterocyclic or carbocyclic ring.

Preferably, the platinum complex is a platinum(IV) complex.

The platinum complex can be present in form of a salt, i.e. suitable counterions may be present or in form of a solvate. A counterion might affect the solubility or other chemical or physical properties of the platinum complex, wherein the exact nature of the counterion is not critical. The counterion is preferably pharmaceutically acceptable, i.e. not with therapeutically relevant toxicity in the amounts used. Counterions can in particular be anions which are unlikely to bind directly to the platinum center, i.e. non-coordinating anions.

As used herein, the term "solvate" refers to a complex of variable stoichiometry formed by a solute, i.e. the complex, and a solvent. If the solvent is water, the solvate formed is a hydrate.

R is fluorophore moiety and comprises an aromatic part with a delocalized, conjugated π-electron system. The term "fluorophore moiety" as used herein refers to a functional part of the platinum complex which can allow the platinum complex or molecule absorb light at a given wavelength and emit light at another wavelength upon excitation. The fluorophore moiety of the present invention can act as a photosensitive functional moiety which can produce reactive oxygen species such as but not limited to singlet oxygen upon photoexcitation. In particular, the fluorophore moiety may be derived from a fluorophore compound, including, but not limited to, porphyrin, fluorescein, rhodol, rhodamine, coumarin, boron-dipyrromethenes (BODIPY) and their derivatives, and other commercially available fluorescent molecules.

Preferably the fluorophore moiety of the platinum complex is capable of absorbing light at a wavelength within the visible spectrum, from about 400 nm to about 750 nm, from about 400 nm to about 600 nm, from about 460 nm to about 550 nm, from about 600 nm to about 750 nm, from about 620 nm to about 680 nm, about 620 nm, or about 650 nm.

The linker group L is an organic unit of any lengths comprising atoms or groups to link, i.e. to connect, two parts of the platinum complex of the present invention, namely the 'platinum part' of the platinum complex and the 'aromatic part' of R together. Non-limiting examples include a straight chain or branched alkanediyl or alkenediyl chain. In particular embodiments of the present invention, L is $-(CH_2)_m-$, wherein m is an integer which is ≥0 for example m is 0, 1, 2, or 3.

M in the structure of Formula (II) is $H_2$ or a metal atom. The metal atom may be selected from iron, cobalt, nickel, copper, zinc, titanium, vanadium, chromium, manganese, molybdenum, zirconium, cadmium, antimony, niobium, palladium or platinum; preferably selected from iron, nickel, copper, zinc or manganese. In an embodiment, M is $H_2$ which means two hydrogen atoms are provided to bond to two nitrogen atoms in the adjacent nitrogen-containing five-membered rings to form —NH bonding, i.e. forming pyrroles.

$R_1$ to $R_{11}$ are independently a substituent or a hydrogen atom. The substituent can be, for example, but not limited to, a hydrocarbon group, a nitrogen-containing group, a heterocyclic group, an oxygen-containing group, a phosphorous-containing group, a sulfur-containing group or a halogen atom or the like, wherein an adjacent pair of $R_1$ to $R_{11}$ may form a fused heterocyclic or carbocyclic ring.

An electron donor ligand means a ligand which is electron donating, i.e. has a donor atom with electron-donating ability such as a nitrogen atom, an oxygen atom, a phosphorous (P) atom or a sulfur atom. Non-limiting examples of electron donor ligands are nitrogen-containing ligands, oxygen-containing ligands, phosphorous-containing ligands, sulfur-containing ligands and halogen containing ligands. Electron donor ligands can, for example, include, imine, aqua, halido (i.e. halide ions in particular including chlorido, bromido or fluorido), amines, diamines, triamines, ammine ($NH_3$), alkyl, cyanido, nitrato, hydroxido, alkoxy, phenoxy, anions of an alkyl mono- or poly-, such as di-, carboxylic acid such as oxalato or dianions of glycolic acid, an alcoholato ligand, alkylthio, thiolato, phosphito, phosphane, β-diketone, nitrato, a heterocycle such as pyridine or 2-methylpyridine. The term "alkyl" as used herein refers to saturated, straight-chain or branched hydrocarbons which may, for example, contain between 1 and 20 carbon atoms such as 1 to 5 carbon atoms. The electron donor ligands in particular include ammine (NH$_3$), aqua, halido such as chlorido, hydroxido, oxalato, diamines such as 1,2-cyclohexanediamine. Y, Y', X, X' and Z may optionally be linked to each other in any combination to form polydentate ligands, in particular bidentate ligands.

In an embodiment of the present invention, X, X', Y, Y' and Z are independently selected from a nitrogen-containing ligand, an oxygen-containing ligand, a phosphorous-containing ligand, a sulfur-containing ligand or a halogen containing ligand, in particular from ammine, hydroxido, halido, oxalato or diamines, or —OR. In a particular embodiment, X and X' are linked to each other to form a first bidentate ligand and/or Y and Y' are linked to each other to form a second bidentate ligand. In a particular embodiment, Z is hydroxido or —OR preferably is hydroxido. In another particular embodiment, Z is not —OR.

n is zero or any positive or any negative charge. In an embodiment of the present invention n is 0 or 1.

In an embodiment, the platinum complex of the present invention comprises a structure of Formula (IV)

Formula (IV)

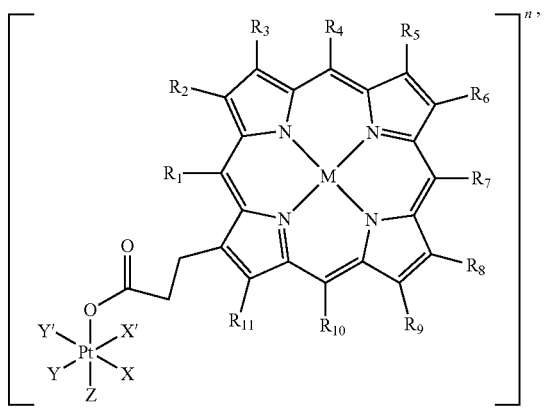

wherein X, X', Y, Y', Z, n and R$_1$ to R$_{11}$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is H$_2$, or a metal atom selected from iron, nickel, copper, zinc or manganese, or preferably M is H$_2$; and R$_1$ to R$_{11}$ are independently selected from a hydrogen atom, a hydrocarbon group, a nitrogen-containing group, a heterocyclic group, an oxygen-containing group, a phosphorous-containing group, a sulfur-containing group or a halogen atom, preferably R$_1$ and R$_2$ form a fused 5-membered cycloalkanone, and R$_3$ to R$_{11}$ are independently selected from a hydrogen atom, a saturated or unsaturated C1-C3 alkyl group unsubstituted or substituted with a hydroxy group or a halogen.

In a preferred embodiment, the platinum complex of the present invention comprises a structure of Formula (Va) or particularly Formula (Vb):

Formula (Va)

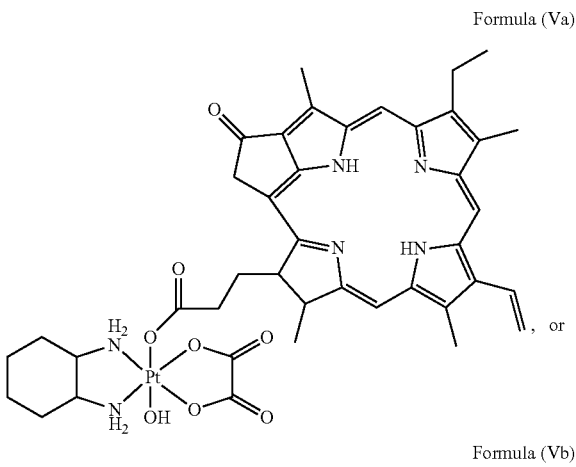

, or

Formula (Vb)

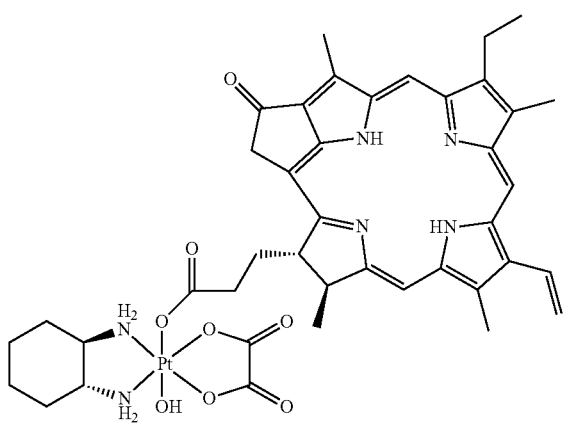

In an embodiment, the platinum complex of the present invention comprises a structure for Formula (VI)

Formula (VI)

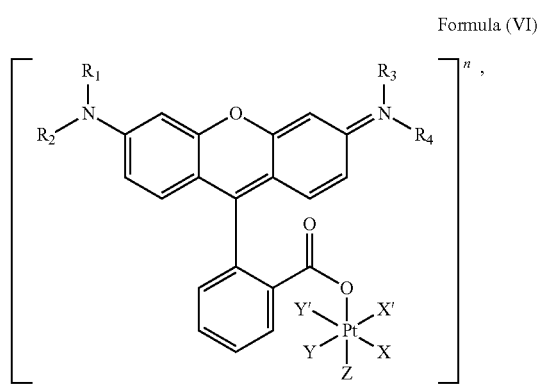

wherein X, X', Y, Y', Z, n and R$_1$ to R$_4$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is H$_2$, or a metal atom selected from iron, nickel, copper, zinc or manganese, or preferably M is H$_2$; and $R_1$ to $R_4$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$, $R_2$, $R_3$ and $R_4$ are independently selected from a hydrogen atom, a saturated or unsaturated C1-C3 alkyl group unsubstituted or substituted with a hydroxy group or a halogen, and/or $R_1$, $R_2$, $R_3$ and $R_4$ identical, or more preferably or $R_1$, $R_2$, $R_3$ and $R_4$ are ethyl groups.

In a preferred embodiment, the platinum complex of the present invention comprises a structure of Formula (VIIa) or particularly Formula (VIIb):

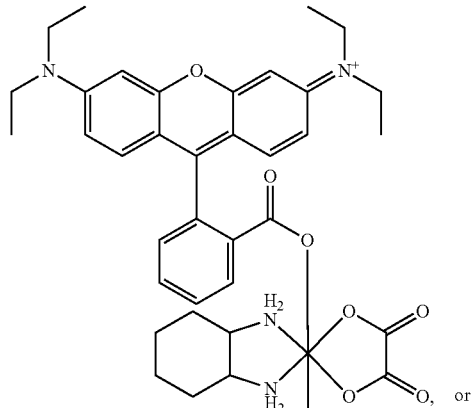

Formula (VIIa)

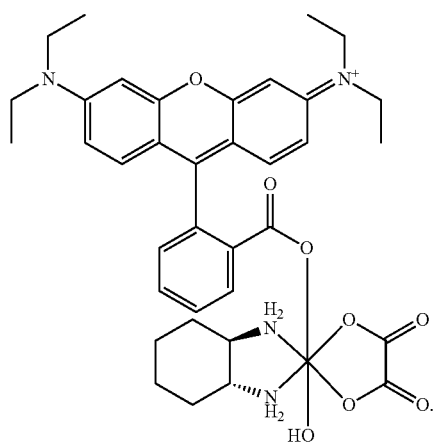

Formula (VIIb)

Further provided with the present invention is a method for preparing the platinum complex described above, i.e. for preparing a platinum complex comprising a structure of Formula (I):

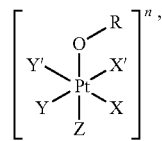

Formula (I)

with X, X', Y, Y' and Z, n and R as defined above.

The method comprises linking a platinum complex precursor which is in particular a platinum(IV) complex precursor and which comprises a structure of Formula (VIII):

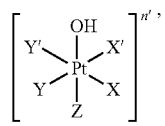

Formula (VIII)

with a fluorophore moiety R to form the platinum complex as described above, wherein X, X', Y, Y' and Z are as defined above, n' means zero or any positive or negative charge and wherein R is comprises a structure of Formula (II) or Formula (III):

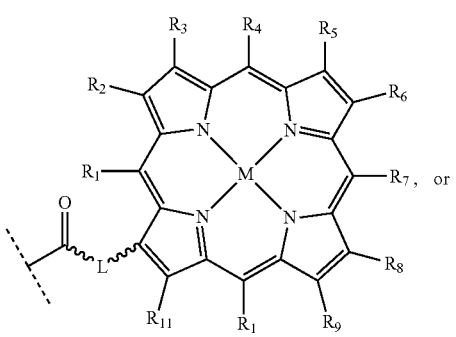

Formula (II)

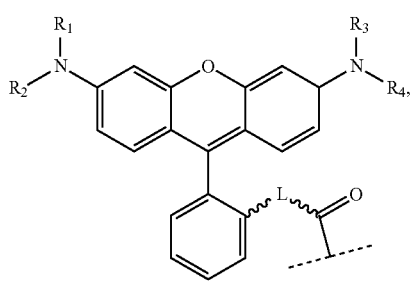

Formula (III)

and wherein L, M and $R_1$ to $R_{11}$ are as defined above.

The platinum complex precursor in particular platinum (IV) complex precursor can comprise a structure of Formula (VIIII):

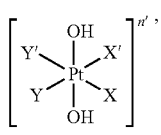

Formula (VIIII)

i.e. Z is hydroxido.

Particular platinum complex precursor comprises a structure of Formula (X):

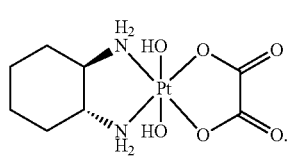

Formula (X)

In an embodiment of the present invention, the method is suitable for preparing a platinum complex of Formula (I) with R having a structure of Formula (II)

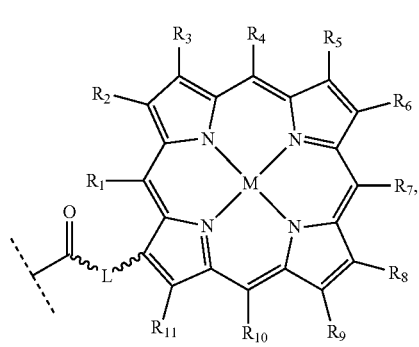

Formula (II)

wherein X, X', Y, Y', Z, M, L, n and $R_1$ to $R_{11}$ are as defined above.

The method comprises steps of:

(i) optionally preparing a hydroxysuccinimide(NHS)-ester of a fluorophore compound having a part of structure of Formula (II), preferably the fluorophore compound is a porphyrin or its derivative such as pyropheophorbide a;

(ii) reacting a platinum complex precursor of Formula (VIII) such as of Formula (VIIII) or in particular of Formula (X) with the N-hydroxysuccinimide(NHS)-ester of the fluorophore compound; and (iii) isolating the platinum complex of Formula (I) and optionally purifying the platinum complex.

Step (ii) in particular comprises:

a) preparing a mixture of the platinum complex precursor and the NHS-ester in a reaction solvent;

b) stirring the mixture after step a) for at least about 8 h at a temperature of at least about 20° C.

"Isolating" the platinum complex means at least partially separating the platinum complex from other components such as side products, the reactants and the solvent present in the reaction mixture after step (ii). Step (iii) in particular comprises filtering the mixture for obtaining a filtrate, subjecting the mixture to centrifugation, allowing the platinum complex to form precipitate in water such as cold water, adding a precipitation solvent to the filtrate for obtaining a precipitate and washing the precipitate with a washing solvent.

The reaction solvent in step a) is preferably dimethyl sulfoxide (DMSO). In particular, the NHS-ester is added in step a) in form of a mixture with at least a part of the reaction solvent, in particular DMSO.

The purification step in step (iii) may be performed by column chromatograph such as silica-gel column chromatography, recrystallization or the like.

In particular, the method is suitable for preparing a platinum complex, preferably a photo-activatable platinum complex, comprising a structure of Formula (IV)

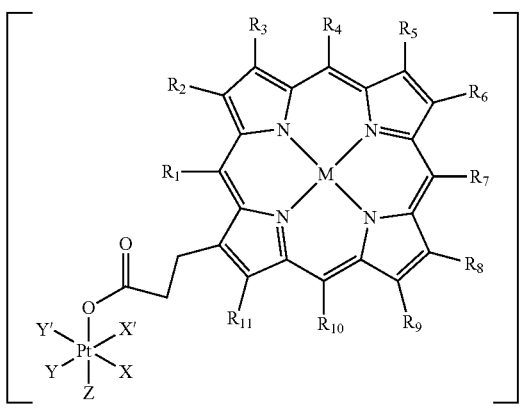

Formula (IV)

wherein X, X', Y, Y', Z, n and $R_1$ to $R_{11}$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is $H_2$, or a metal atom selected from iron, nickel, copper, zinc or manganese, or preferably M is $H_2$; and $R_1$ to $R_{11}$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$ and $R_2$ form a fused 5-membered cycloalkanone, and $R_3$ to $R_{11}$ are independently selected from a hydrogen atom, a saturated or unsaturated C1-C3 alkyl group unsubstituted or substituted with a hydroxy group or a halogen.

Preferably, the platinum complex prepared comprises a structure of Formula (Va) or particularly Formula (Vb):

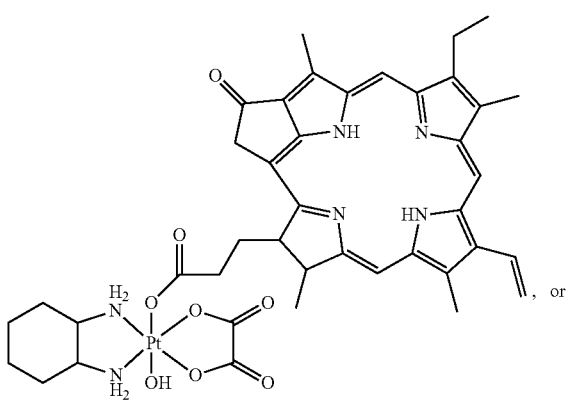

Formula (Va)

, or

-continued

Formula (Vb)

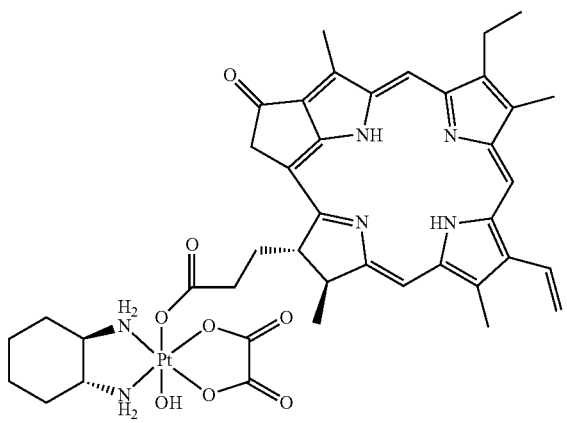

In another embodiment of the method of the present invention, the method is suitable for preparing a platinum complex, preferably a photo-activatable platinum complex, of Formula (I) with R having a structure of Formula (III)

Formula (III)

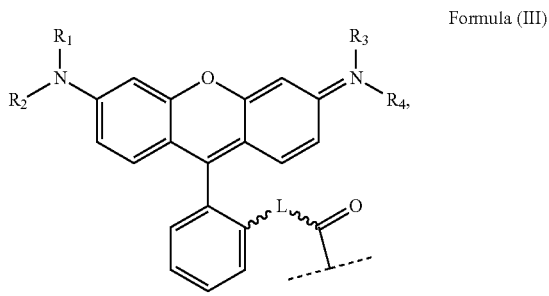

wherein X, X', Y, Y', Z, L, n and $R_1$ to $R_4$ are as defined above.

The method comprises steps of:

(i) optionally preparing a hydroxysuccinimide(NHS)-ester of a fluorophore compound having a part of structure of Formula (III), preferably the fluorophore compound is a rhodamine or its derivative;

(ii) reacting a platinum complex precursor of Formula (VIII) such as of Formula (VIIII) or in particular of Formula (X) with the N-hydroxysuccinimide(NHS)-ester of the fluorophore compound; and (iii) isolating the platinum complex of Formula (I) and optionally purifying the platinum complex.

Step (ii) in particular comprises:

a) preparing a mixture of the platinum complex precursor and the NHS-ester in a reaction solvent;

b) stirring the mixture after step a) for at least about 8 h at a temperature of at least about 20° C.

Step (iii) in particular comprises filtering the mixture for obtaining a filtrate, subjecting the mixture to centrifugation, allowing the platinum complex to form precipitate in water such as cold water, adding a precipitation solvent to the filtrate for obtaining a precipitate and washing the precipitate with a washing solvent.

The reaction solvent in step a) is preferably N, N'-dicyclohexylcarbodiimide (DCC). In particular, the NHS-ester is added in step a) in form of a mixture with at least a part of the reaction solvent, in particular DCC.

The purification step in step (iii) may be performed by column chromatograph such as silica-gel column chromatography, recrystallization or the like.

In particular, the method is suitable for preparing a platinum complex, preferably a photo-activatable complex, comprising a structure of Formula (VI)

Formula (VI)

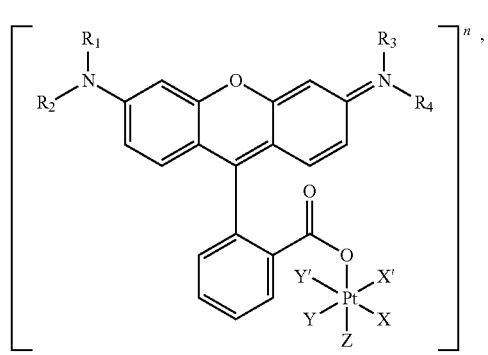

wherein X, X', Y, Y', Z, n and $R_1$ to $R_4$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is $H_2$, or a metal atom selected from iron, nickel, copper, zinc or manganese, or preferably M is $H_2$; and $R_1$ to $R_4$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$, $R_2$, $R_3$ and $R_4$ are independently selected from a hydrogen atom, a saturated or unsaturated C1-C3 alkyl group unsubstituted or substituted with a hydroxy group or a halogen, and/or $R_1$, $R_2$, $R_3$ and $R_4$ identical, or more preferably or $R_1$, $R_2$, $R_3$ and $R_4$ are ethyl groups.

Preferably, the platinum complex prepared comprises a structure of Formula (VIIa) or particularly Formula (VIIb):

Formula (VIIa)

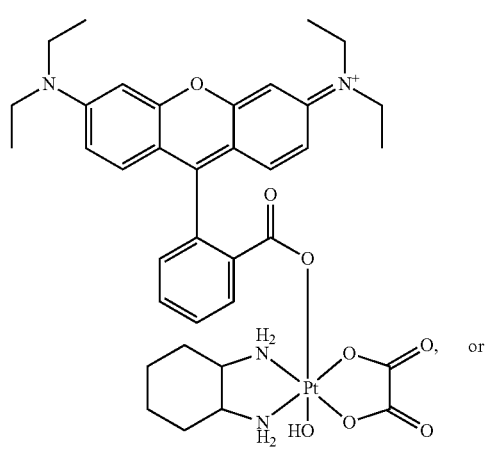

or

-continued

Formula (VIIb)

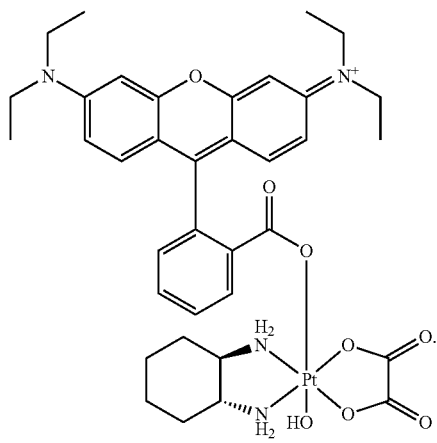

The present invention in a third aspect pertains to a method for treating a subject suffering from cancer comprising the step of administering an effective amount of the platinum complex as described above to the subject, i.e. comprising the step of administering a platinum complex comprising a structure of Formula (I) to the subject:

Formula (I)

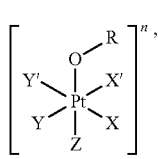

with X, X', Y, Y' and Z, n and R as defined above.

The cancer is in particular, for example, but not limited to one of:
an ovarian cancer,
a lung cancer,
a breast cancer, or
a colorectal cancer.

The terms "cancer" and "cancerous" describe a physiological condition in subjects in which a population of cells are characterized by unregulated malignant (cancerous) cell growth. The cancer can be a cancer which has a natural, i.e. intrinsic, or acquired resistance against one or more chemotherapeutic compounds in particular which has a natural or has an acquired, i.e. developed resistance against known coordination complexes of platinum such as cisplatin. A cancer is resistant against one or more chemotherapeutic compounds if it comprises cancer cells which are resistant against said chemotherapeutic compounds. Accordingly, the cancer cells with a resistant phenotype will be less sensitive or more tolerant to the one or more chemotherapeutic compounds. Such cancer or cancer cells can be detected in a subject, cancer or tissue by administering to the subject, tissue, or cell, the one or more chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have the resistance against the chemotherapeutic compound or non-cancerous cells. This can be determined, for example, by means of an MTT assay. A cancer or cancer cells which have a natural (intrinsic) or acquired resistance against cisplatin are referenced herein as "cisplatin-resistant".

In particular embodiments of the present invention, the cancer has a natural or an acquired resistance against cisplatin, also known as cDDP (cis-diamminedichloroplatinum).

The term "subject" used herein refers to a living organism and can include but is not limited to a human, a plant and an animal. The subject is preferably a human or an animal, in particular the subject is a mammal, preferably a human.

In an embodiment of the present invention, the administered platinum complex comprising a structure of Formula (IV)

Formula (IV)

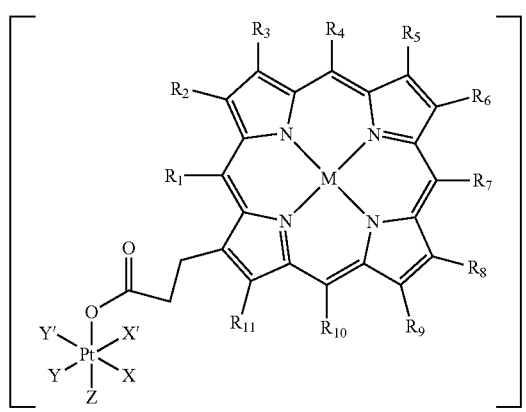

wherein X, X', Y, Y', Z, n and $R_1$ to $R_{11}$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is $H_2$, or a metal atom selected from iron, nickel, copper, zinc or manganese, or preferably M is $H_2$; and $R_1$ to $R_{11}$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$ and $R_2$ form a fused 5-membered cycloalkanone, and $R_3$ to $R_{11}$ are independently selected from a hydrogen atom, a saturated or unsaturated C1-C3 alkyl group unsubstituted or substituted with a hydroxy group or a halogen.

Preferably, the administered platinum complex comprises a structure of Formula (Va) or particularly Formula (Vb):

Formula (Va)

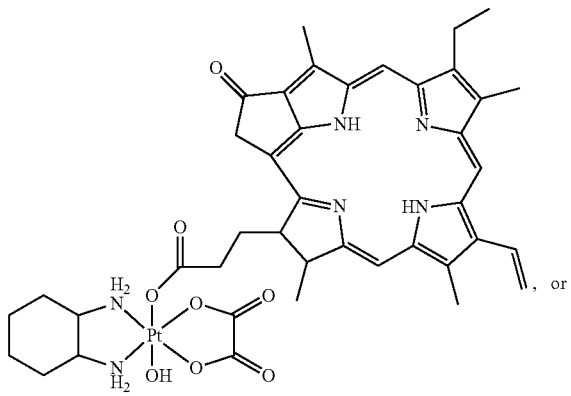

, or

Formula (Vb)

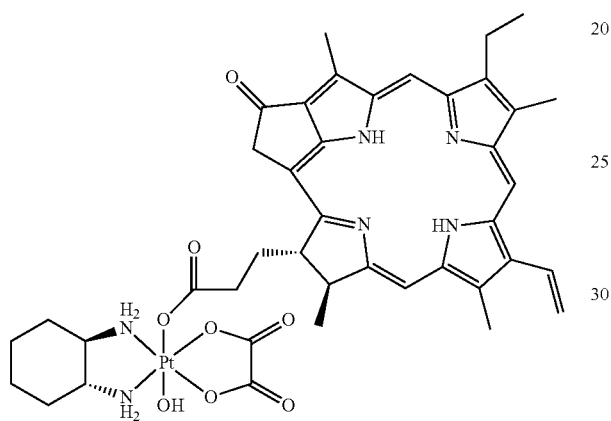

The platinum complex can be, for example, present in form of a pharmaceutically acceptable salt or a solvate.

In another embodiment of the present invention, the administered platinum complex comprising a structure of Formula (VI):

Formula (VI)

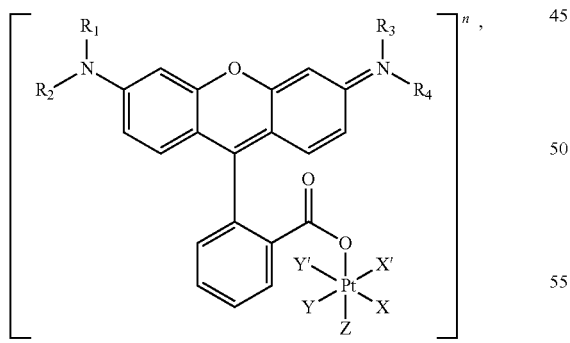

wherein X, X', Y, Y', Z, n and $R_1$ to $R_4$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is $H_2$, or a metal atom selected from iron, nickel, copper, zinc or manganese, or preferably M is $H_2$; and $R_1$ to $R_4$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$, $R_2$, $R_3$ and $R_4$ are independently selected from a hydrogen atom, a saturated or unsaturated C1-C3 alkyl group unsubstituted or substituted with a hydroxy group or a halogen, and/or $R_1$, $R_2$, $R_3$ and $R_4$ identical, or more preferably or $R_1$, $R_2$, $R_3$ and $R_4$ are ethyl groups.

Preferably, the administered platinum complex comprises a structure of Formula (VIIa) or particularly Formula (VIIb):

Formula (VIIa)

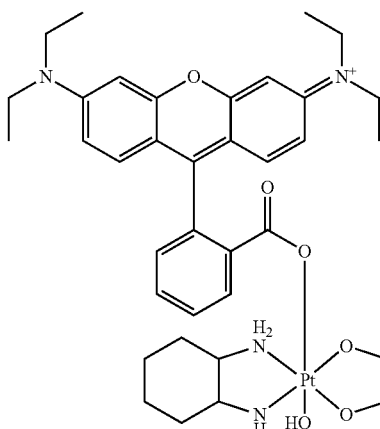

, or

Formula (VIIb)

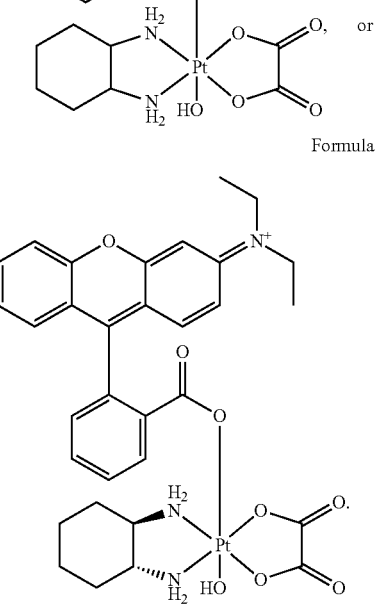

The platinum complex can also be, for example, present in form of a pharmaceutically acceptable salt or a solvate.

The expression "effective amount" and "effective dose" generally denote an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells.

The effective amount of the platinum complex of the present invention may depend on the species, body weight, age and individual conditions of the subject and can be determined by standard procedures such as with cell cultures or experimental animals. A concentration of the platinum complex may, for example, be at least about 10 nm.

The platinum complex can be present in solid, semisolid or liquid form. The platinum complex of the present invention can be administered by an oral, topical or parenteral route to the subject, in particular by an oral route or an intravenous route.

The platinum complex may be administered in form of a pharmaceutical composition comprising the platinum complex and a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof. "Pharmaceutically tolerable excipients" are those which can be taken by the subject without therapeutically relevant adverse effects and do not negatively influence the efficiency of the platinum complex. A person of skill in the art is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition can be present in solid, semisolid or liquid form to be administered by an oral or parenteral route to the subject.

In a preferred embodiment, the method further comprises the steps of:

locating a target area on the subject for exposure of light with a defined wavelength; and applying the light to the target area.

In particular, the platinum complex is applied as a therapeutic agent in a photodynamic therapy. The term "target area" refers to a part on the subject where close to cancer cells or cancerous tissues in the subject and/or treatment is required to alleviate the symptoms or illness caused by the disease. The target area may be located topically or inside the body of the subject. After the step of administering an effective amount of the platinum complex to the subject for a certain period of time, the target area on the subject is located, and light with a defined wavelength is applied to the target area so as to activate the fluorophore moiety of the platinum complex to absorb the light for subsequent photochemical reaction.

Preferably the fluorophore moiety of the platinum complex is capable of absorbing light at a wavelength within the visible spectrum, from about 400 nm to about 750 nm, from about 400 nm to about 600 nm, from about 460 nm to about 550 nm, from about 600 nm to about 750 nm, from about 620 nm to about 680 nm, about 620 nm, or about 650 nm.

In an embodiment where R has a structure of Formula (II) or Formula (III), the fluorophore moiety may be activated by light with a wavelength of about 400 nm to about 750 nm, preferably about 600 nm to about 750 nm or about 400 nm to about 600 nm.

In an embodiment where the platinum complex comprises a structure of Formula (IV) in particular of Formula (Va) or Formula (Vb) as defined above, the platinum complex releases a compound of Formula (XI):

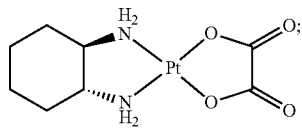

Formula (XI)

and/or generates reactive oxygen species such as singlet oxygen and hydroxyl radical upon excitation of light with a wavelength of about 600 nm to about 750 nm, preferably about 620 nm to about 680 nm. The compound of Formula (XI) is known as oxaliplatin and has inhibitory effect against cancer cells.

In an embodiment where the platinum complex comprises a structure of Formula (VI) in particular of Formula (VIIa) or Formula (VIIb), the platinum complex releases a compound of Formula (XI):

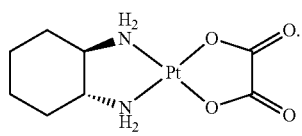

Formula (XI)

and/or generates reactive oxygen species such as singlet oxygen and hydroxyl radical upon excitation of light with a wavelength of about 400 nm to about 600 nm, preferably about 460 nm to about 550 nm.

Accordingly, the platinum complex of the present invention may act as a prodrug, which is exceptionally suitable in a targeted therapy including immunotherapy such as monoclonal antibody therapy, to release the active part such as the compound of Formula (X) for achieving the therapeutic effect and/or results in synergistic effect by the platinum complex and/or the products formed after excitation. In an embodiment, the platinum complex is a platinum(IV) complex which can release a platinum(IV) drug for therapeutic use.

In particular, the platinum complexes of the present invention which prepared from a platinum complex precursor of Formula (VIIII) in particular of Formula (X), as defined above, are exceptionally suitable for treatment of cancer as well as inhibition in cancer cells.

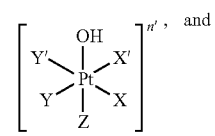

Formula (VIIII)

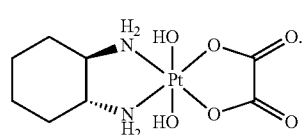

Formula (X)

Without wishing to be limited by theory, in an embodiment, the platinum complex of the present invention is found to be effective in treatment of cancer as it can produce an active compound such as of Formula (XI) as defined above upon excitation of light with a defined wavelength. This is particularly advantageous as the platinum complex can reduce or prevent severe or undesirable side effects caused by the active compound to non-target area on the subject receiving the treatment.

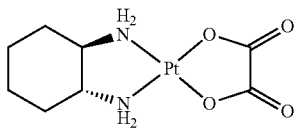

Formula (XI)

Preferably, the light with a defined wavelength is applied to the target area at a power density of about 0.1 mW/cm$^2$ to about 50 mW/cm$^2$, about 1 mW/cm$^2$ to about 25 mW/cm$^2$, about 2 mW/cm$^2$ to about 20 mW/cm$^2$, about 3 mW/cm$^2$ to about 15 mW/cm$^2$, or about 5 mW/cm$^2$ to about 10 mW/cm$^2$. In an embodiment, the light is applied to the target area at a power density of about 5 mW/cm$^2$ to about 10 mW/cm$^2$, preferably 7 mW/cm$^2$.

The IC$_{50}$ of the platinum complex towards cancer cells is preferably at most 1000 nM, in particular it is less than 500 nM and further preferred less than 200 nM and most preferably less than 200 nM with irradiation for about or at least 15 min in particular towards cancer cells from one of an ovarian cancer, a lung cancer, a breast cancer, or a colorectal cancer including cisplatin resistant cancer.

The Resistant Factor of the platinum complex of the present invention towards cisplatin-resistant cancer cells is preferably less than 10, more preferably less than 8 and in particular even less than 5. The Resistant Factor is calculated by dividing the IC$_{50}$ of the platinum complex towards cisplatin-resistant cells by its IC$_{50}$ towards cancer cells of the same cell type or tissue which do not have a cisplatin-resistant phenotype.

It would be appreciated that the method may be performed in combination with other therapeutically effective treatments such as one or more of:
  other therapeutically effective compounds such as chemotherapeutic compounds including, for example, a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog;
  radiation therapy; and/or
  hormonal therapy.

The present invention further provides a pharmaceutical composition comprising:
  (i) a platinum complex of the present invention; and
  (ii) a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof. The pharmaceutical composition can be present in solid, semisolid or liquid form to be administered by an oral or parenteral route to a subject.

According to the invention is also the platinum complex described above, in particular of Formula (IV) such as of Formula (Va) or Formula (Vb), or of Formula (VI) such as of Formula (VIIa) or Formula (VIIb), for use as a medicament for the treatment of cancer or for use in the preparation of a medication for treatment of cancer. The platinum complex can be used in an effective amount for treating an animal or a human, in particular mammal, preferably a human. In an embodiment, the platinum complex may be used a medicament for a photodynamic treatment of cancer.

In another aspect, the invention provides a method for inhibiting the growth of cancer cells. The method comprises the step of contacting a population of cancer cells with the platinum complex described above which can, for example, be a salt or solvate. Preferably, the cell growth is reduced and/or cell death is induced. MTT assay can be used for confirming the effect on cell death and cell viability.

For example, inhibiting the growth of cancer cells can mean a decrease in the cell viability in particular a significant decrease and/or an increase in the number of apoptotic cells, in particular a significant increase. The skilled person is aware of methods for verifying such effects such as with cell viability measurement by means of a MTS proliferation assay, a MTT assay or by determination of the apoptosis rate by means of Annexin V flow cytometry measurement. As used herein, the term "significant" means that is statistically significant as determined by Student's t-test or other art-accepted measures of statistical significance.

In an embodiment of the present invention, the administered platinum complex comprising a structure of Formula (IV)

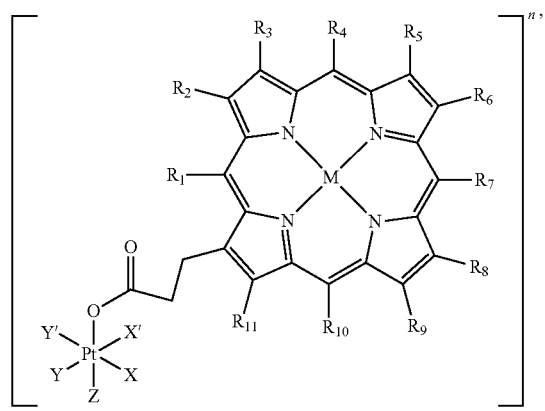

Formula (IV)

wherein X, X', Y, Y', Z, n and R$_1$ to R$_{11}$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is H$_2$, or a metal atom selected from iron, nickel, copper, zinc or manganese, or preferably M is H$_2$; and R$_1$ to R$_{11}$ are independently selected from a hydrogen atom, a hydrocarbon group, a nitrogen-containing group, a heterocyclic group, an oxygen-containing group, a phosphorous-containing group, a sulfur-containing group or a halogen atom, preferably R$_1$ and R$_2$ form a fused 5-membered cycloalkanone, and R$_3$ to R$_{11}$ are independently selected from a hydrogen atom, a saturated or unsaturated C1-C3 alkyl group unsubstituted or substituted with a hydroxy group or a halogen.

Preferably, the administered platinum complex comprises a structure of Formula (Va) or particularly Formula (Vb):

Formula (Va)

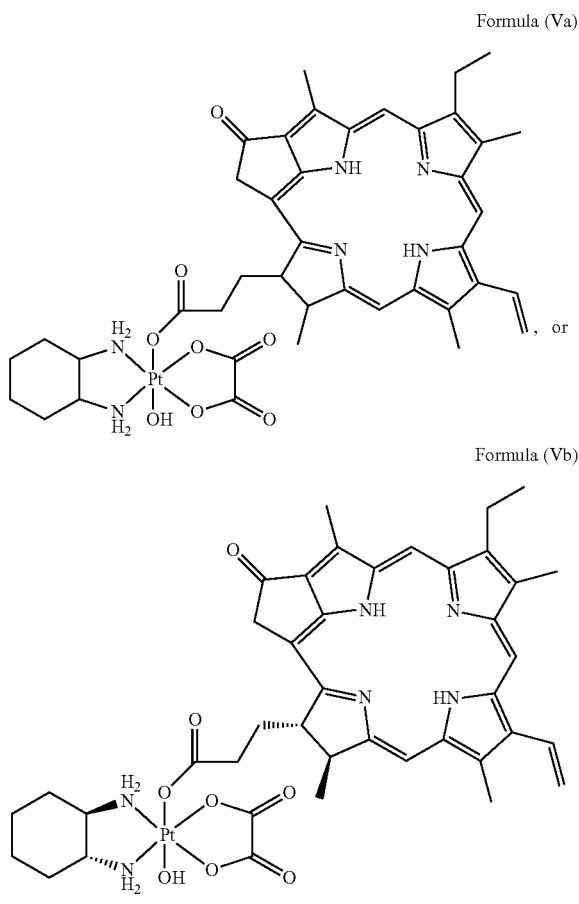

Formula (Vb)

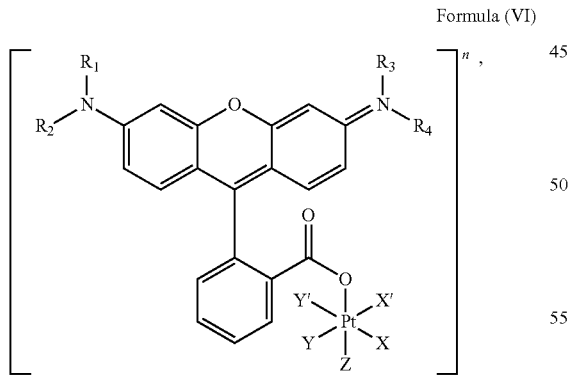

The platinum complex can be, for example, present in form of a salt or a solvate.

In another embodiment of the present invention, the administered platinum complex comprising a structure of Formula (VI):

Formula (VI)

$$\left[ \begin{array}{c} \text{structure} \end{array} \right]_n,$$

wherein X, X', Y, Y', Z, n and $R_1$ to $R_4$ are as defined above. In particular, X, X', Y, Y' and Z are independently selected from ammine, hydroxido, halido, oxalato or diamines, or —OR, preferably X and X' are linked to form a first bidentate ligand, Y and Y' are linked to form a second bidentate ligand, and Z is hydroxido or —OR, or more preferably X and X' are linked to form oxalato, and Y and Y' are linked to form diamines, and Z is hydroxido;

M is $H_2$, or a metal atom selected from iron, nickel, copper, zinc or manganese, or preferably M is $H_2$; and $R_1$ to $R_4$ are independently selected from a hydrogen atom, a hydrocarbon group, a nitrogen-containing group, a heterocyclic group, an oxygen-containing group, a phosphorous-containing group, a sulfur-containing group or a halogen atom, preferably $R_1$, $R_2$, $R_3$ and $R_4$ are independently selected from a hydrogen atom, a saturated or unsaturated C1-C3 alkyl group unsubstituted or substituted with a hydroxy group or a halogen, and/or $R_1$, $R_2$, $R_3$ and $R_4$ identical, or more preferably or $R_1$, $R_2$, $R_3$ and $R_4$ are ethyl groups.

Preferably, the administered platinum complex comprises a structure of Formula (VIIa) or particularly Formula (VIIb):

Formula (VIIa)

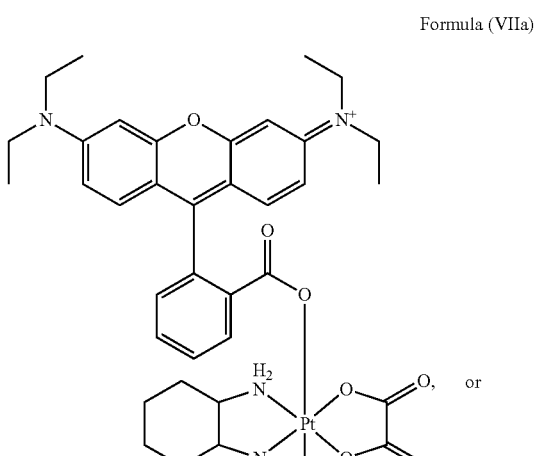

Formula (VIIb)

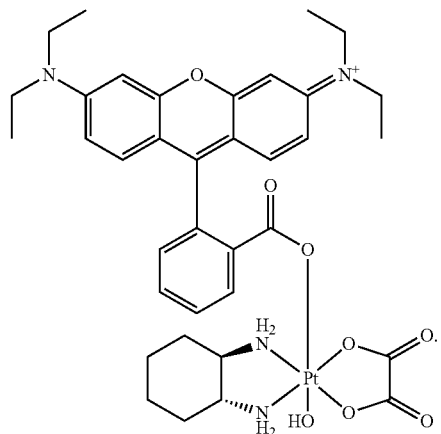

The platinum complex can also be, for example, present in form of a salt or a solvate.

The cancer cells, for example, but not limited are from one of:

an ovarian cancer,
a lung cancer,
a breast cancer, or
a colorectal cancer.

The cancer cells can have a natural or an acquired resistance against one or more chemotherapeutic compounds, in particular a natural or an acquired resistance against known coordination complexes of platinum such as cisplatin. Preferably, the $IC_{50}$ of the platinum complex towards the cancer cells is less than 500 nM and further preferred less than 200 nM and most preferably less than 200 nM with irradiation for about or at least 15 min in particular towards one of an ovarian cancer, a lung cancer, a breast cancer, or a colorectal cancer including cisplatin-resistant cancers. The Resistant Factor of the platinum complex of the present invention towards cisplatin-resistant cancer cells is preferably less than 8, less than 5 in particular even less than 3.

The step of contacting the tumor cells with the platinum complex of the present invention may be carried out by applying an incubation solution comprising the platinum complex to said cells which incubation solution may further comprise suitable excipients such as buffers or a suitable growth medium. Alternatively, contacting the cancer cells with the platinum complex of the present invention can be carried out by administering the platinum complex to a subject such as a mammal like a human, for example, by an oral or parenteral route in form of a pharmaceutical composition as described above.

Preferably, the method further comprises the step of exposing the cancer cells with light having a defined wavelength. The fluorophore moiety of the platinum complex is capable of absorbing light at a wavelength within the visible spectrum, from about 400 nm to about 750 nm, from about 400 nm to about 600 nm, from about 460 nm to about 550 nm, from about 600 nm to about 750 nm, from about 620 nm to about 680 nm, about 620 nm, or about 650 nm.

Preferably, the light with a defined wavelength is applied to the target area at a power density of about 0.1 mW/cm² to about 50 mW/cm², about 1 mW/cm² to about 25 mW/cm², about 2 mW/cm² to about 20 mW/cm², about 3 mW/cm² to about 15 mW/cm², or about 5 mW/cm² to about 10 mW/cm². In an embodiment, the light is applied to the target area at a power density of about 5 mW/cm² to about 10 mW/cm², preferably 7 mW/cm².

In an embodiment where the platinum complex comprises a structure of Formula (IV) in particular of Formula (Va) or Formula (Vb) as defined above, the platinum complex releases a compound of Formula (XI):

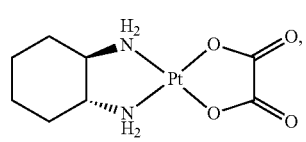

Formula (XI)

and/or generates reactive oxygen species such as singlet oxygen and hydroxyl radical upon excitation of light with a wavelength of about 600 nm to about 750 nm, preferably about 620 nm to about 680 nm.

In an embodiment where the platinum complex comprises a structure of Formula (VI) in particular of Formula (VIIa) or Formula (VIIb), the platinum complex releases a compound of Formula (XI):

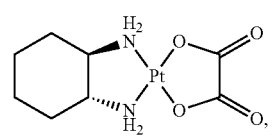

Formula (XI)

and/or generates reactive oxygen species such as singlet oxygen and hydroxyl radical upon excitation of light with a wavelength of about 400 nm to about 600 nm, preferably about 460 nm to about 550 nm.

The examples set out below further illustrate the invention. The preferred embodiments described above and the drawings as well as examples given below represent preferred or exemplary embodiments and a skilled person will understand that the reference to those embodiments or examples is not intended to be limiting.

EXAMPLES

Example 1

Preparation of Complex A

Complex A of the present invention was prepared according to Reaction scheme 1:

Reaction scheme 1

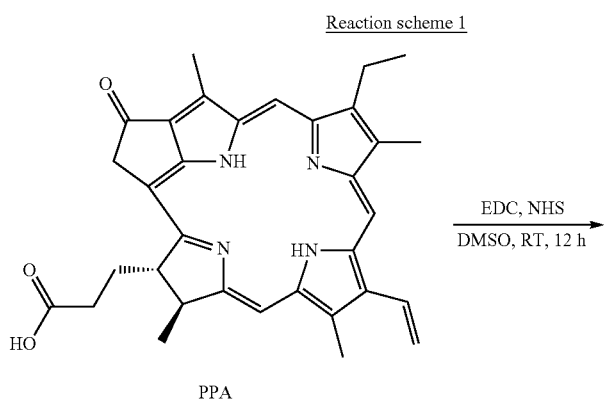

PPA

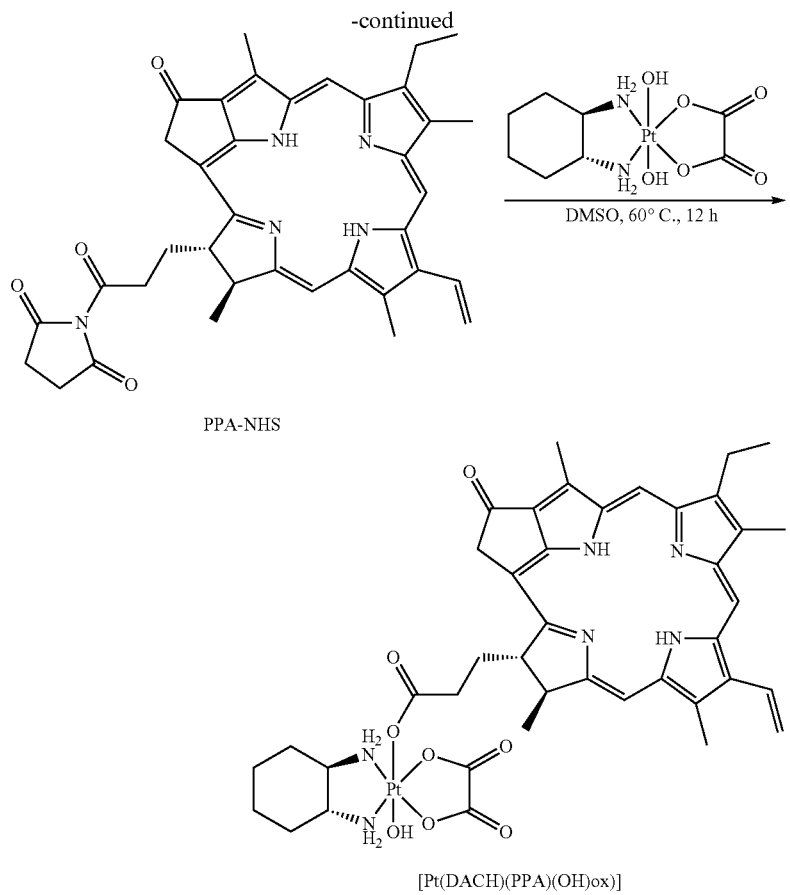

PPA-NHS

[Pt(DACH)(PPA)(OH)ox)]

To the mixture of pyropheophorbide a (PPA, 50 mg, 0.093 mmol) and N-hydroxysuccinimide (NHS, 15 mg, 0.13 mmol) in DMSO (3 mL), 1-ethyl-3-(−3-dimethylaminopropyl) carbodiimide hydrochloride (EDC, 30 mg, 0.15 mmol) were added. The reaction mixture was stirred overnight at room temperature, and then the resulted solution was added to ice-cold 30 mL deionized water dropwise. The precipitate was collected by centrifugation and washed twice by ice-cold water. The precipitate was further lyophilized and redissolved in DMSO (3 mL). Oxaliplatin, i.e. [Pt(DACH)(ox)(OH)$_2$], (40 mg, 0.093, synthesized as described in J. Z. Zhang et al., Chemistry—A European Journal 2013, 19(5), 1672-2676) was added to the solution, and the mixture was stirred at 60° C. overnight. The resulted solution was added to ice-cold 30 mL deionized water dropwise. The obtained precipitate was collected by centrifugation and washed twice by ice-cold deionized water. The final precipitate was lyophilized to get the raw product. The raw product was purified by silica gel column chromatography using MeOH/CH$_2$Cl$_2$ (1:10) as eluent to afford the target complex as black powder—Complex A having the structure of Formula (Vb) was obtained.

NMR spectra of the product were collected on a Bruker Ascend AVANCE III 600 MHz spectrometer. Chemical shifts are reported in parts per million relative to residual solvent peaks. ESI-MS data were obtained on an Agilent API-150EX MS system. Analytical HPLC (RPLC) was conducted on a Shimadzu Prominence LC-20AT HPLC system, equipped with a reversed-phase C18 column (Phenomenex Garmin 250×4.60 mm, 5 μm, 110 Å). The samples were monitored by UV at 254 and 370 nm. Solvent A (H$_2$O with 5% ACN and 0.02% TFA) and solvent B (ACN with 5% H$_2$O and 0.02% TFA) were used for a gradient elution at a flow rate of 1.2 mL/min. The samples were eluted by using program as follow: 0% B (0 min)→20% B (7 min)→100% B (17 min)→100% B (30 min). Platinum content was measured by an Inductively Coupled Plasma-Optical Emission Spectrometer (ICP-OES) (PE Optima 8000). $^1$H NMR (ppm, 600 MHz, DMSO-d$_6$) δ 9.36 (s, 1H), 9.12 (s, 1H), 8.82 (s, 1H), 8.47 (t, J=9.7 Hz, 1H), 8.26 (s, 1H), 8.02 (dd, J=17.8, 11.6 Hz, 1H), 7.91 (s, 1H), 7.31 (t, J=10.0 Hz, 1H), 6.26 (d, J=17.8 Hz, 1H), 6.10 (d, J=12.7 Hz, 1H), 5.19-5.06 (m, 2H), 4.55-4.47 (m, 1H), 4.23 (d, J=10.1 Hz, 1H), 3.46 (s, 3H), 3.45-3.40 (m, 2H), 3.36 (s, 3H), 2.98 (s, 3H), 2.62 (tt, J=19.3, 9.9 Hz, 4H), 2.41 (dd, J=7.3, 5.0 Hz, 1H), 2.09 (d, J=10.5 Hz, 2H), 1.97 (td, J=11.7, 11.2, 6.4 Hz, 1H), 1.74 (d, J=7.3 Hz, 3H), 1.49 (t, J=7.6 Hz, 3H), 1.47 (d, J=8.1 Hz, 3H), 1.39-1.31 (m, 1H), 1.09 (dt, J=22.5, 14.1 Hz, 2H), −0.06 (s, 1H), −2.22 (s, 1H). $^{13}$C NMR (ppm, 151 MHz, DMSO-d$_6$) δ 195.69 (s), 182.20 (s), 172.68 (s), 164.43 (s), 162.19 (s), 154.34 (s), 150.22 (s), 148.34 (s), 144.92 (s), 141.10 (s), 137.44 (s), 136.15 (s), 135.56 (s), 135.25 (s), 132.11 (s), 130.38 (s), 129.42 (s), 128.14 (s), 123.11 (s), 106.36 (s), 104.34 (s), 96.71 (s), 94.22 (s), 62.04 (s), 60.58 (s), 51.76 (s), 49.72 (s), 47.99 (s), 40.89 (s), 34.44 (s), 31.32 (s), 31.21 (s), 31.01 (s), 24.11 (s), 23.37 (s), 18.91 (s), 17.82 (s), 12.39 (s), 12.01 (s), 11.14 (s). $^{195}$Pt NMR (ppm, 129 MHz, DMSO-d$_6$) δ 1406.95 (s). ESI-MS (negative ion mode): m/z [M−H]$^−$: calcd: 946.3; obsd: 946.1. The purity of the compound is 96% as determined by of analytical reversed-phase HPLC (RP-HPLC),

Example 2

Preparation of Complex B

Complex B of the present invention was prepared according to Reaction scheme 2:

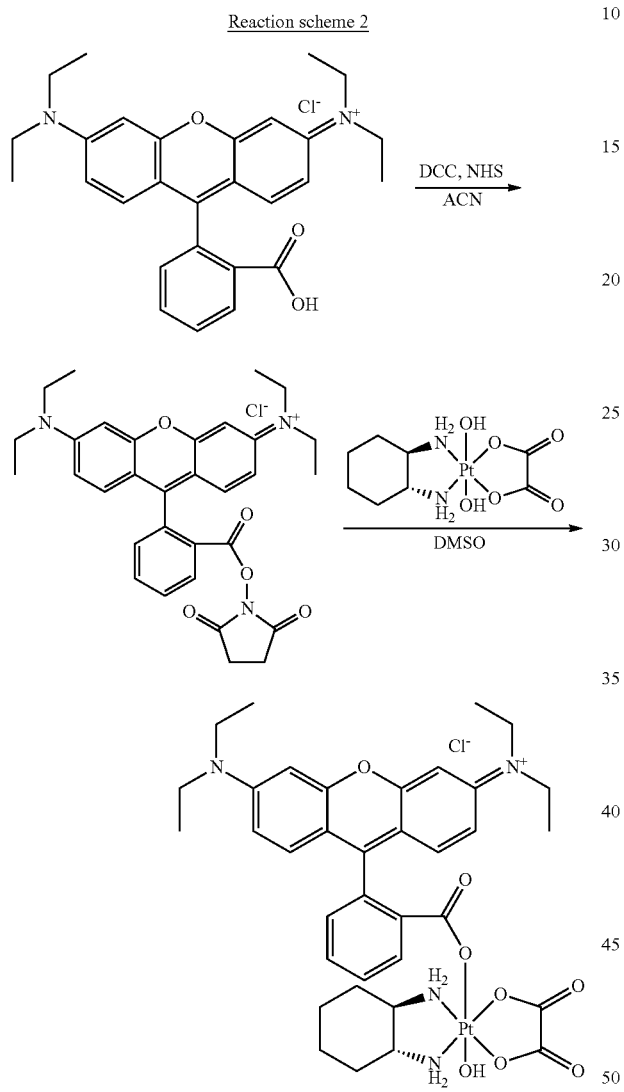

Rhodamine B (0.4 g, 0.84 mmol) was dissolved into 10 mL acetonitrile. Then N-hydroxysuccinimide (NHS, 144 mg, 1.26 mmol) and N, N'-dicyclohexylcarbodiimide (DCC, 207 mg, 1.00 mmol) were added into the solution. The mixture was stirred overnight at room temperature. After that, the byproduct dicyclohexylurea (DCU) was removed by centrifugation and the rhodamine B NHS ester was obtained by vaporizing all the solvent. This rhodamine NHS ester was directly used in the next step without further purification. Rhodamine NHS ester (80 mg, 0.14 mmol) and oxaliplatin (180 mg, 0.41 mmol) were added into 2 mL DMSO. The mixture was stirred at 120° C. for 8 h. After reaction, the unreacted oxaliplatin was removed by centrifugation and the DMSO solution was added into 100 mL cold diethyl ether ($Et_2O$). Red precipitate was thus formed. The red precipitate was collected by filtration followed by washing with 30 mL cold $Et_2O$ twice. After drying in vacuum, the final product—Complex B was obtained as a red solid.

Characterization of the final product was conducted according to the methods as described in Example 1. $^1$H NMR (400 MHz, DMSO) δ 8.37-7.43 (m, 7H), 7.40 (d, J=8.5 Hz, 1H), 7.33-6.81 (m, 6H), 3.96-3.54 (m, 8H), 2.56 (d, J=9.7 Hz, 2H), 2.12-1.89 (m, 2H), 1.57-0.94 (m, 18H).

Example 3

Preparation of Complex C

Complex C of the present invention was prepared according to Reaction scheme 3:

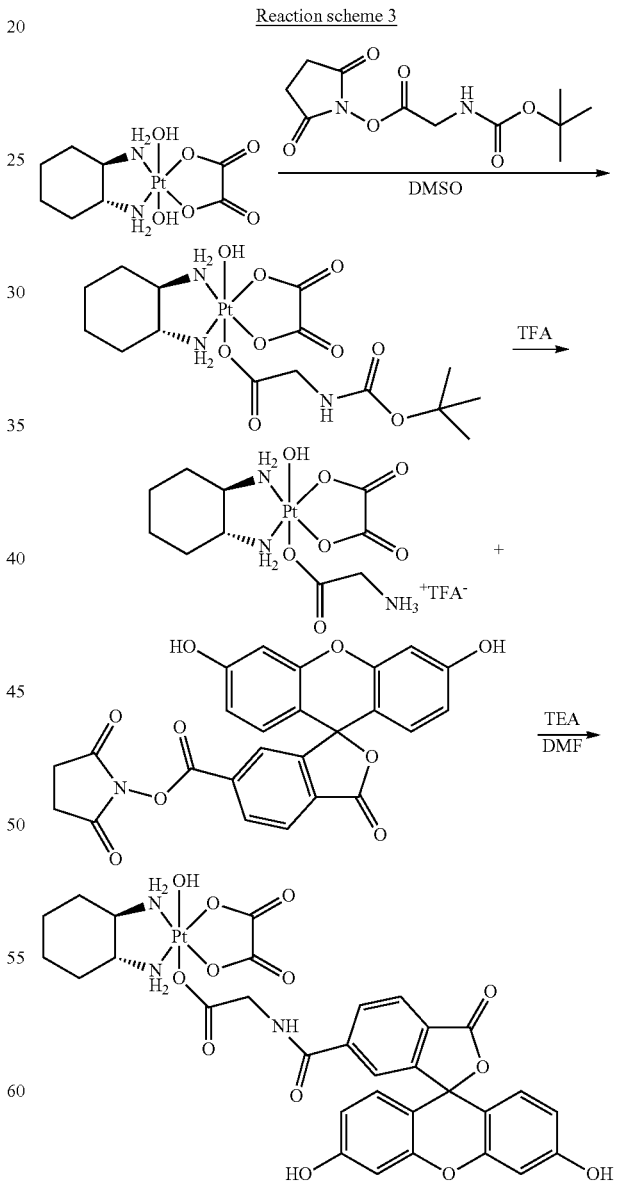

Boc-glycine NHS ester (272 mg, 1 mmol) and oxaliplatin (431 mg, 1 mmol) were added into 2 mL DMSO. The mixture was stirred overnight at 60° C. After reaction, a clear DMSO solution was obtained and the DMSO solution was then added into 100 mL cold $Et_2O$ to induce the formation of precipitate. The white precipitate was collected by centrifugation and then dissolved in a mixture of trifluoroacetic acid (TFA) and dichloromethane (1 mL, v/v, 1:1). This mixture was stirred at room temperature for 30 min. After that, the solvent was vaporized and then the residual was washed with 30 mL $Et_2O$ for twice. After drying in vacuum, [Pt(DACH)(ox)(TFA$^-$ $NH_3^+CH_2COO$)(OH)] was obtained as white solid. [Pt(DACH)(ox)(TFA$^-$ $NH_3^+CH_2COO$)(OH)] (60 mg, 0.1 mmol) was dissolved in 1 mL DMF. 6-Carboxyfluorescein N-hydroxysuccinimide ester (24 mg, 0.05 mmol) and trimethylamine (10 mg, 0.1 mmol) were added into the DMF solution. The mixture was stirred at 70° C. for 6 h and then the DMF solution was added into 10 mL $H_2O$. The yellow precipitate appeared and was isolated by filtering. After drying the precipitate in vacuum, Complex C was obtained as yellow solid.

Characterization of the final product was conducted according to the methods as described in Example 1. $^1$H NMR (400 MHz, DMSO) δ 10.17 (s, 2H), 9.02 (t, J=6.0 Hz, 1H), 8.39 (s, 2H), 8.19 (d, J=8.4 Hz, 1H), 8.10 (d, J=8.0 Hz, 1H), 7.96 (s, 1H), 7.75 (d, J=28.9 Hz, 3H), 6.70 (d, J=1.9 Hz, 2H), 6.66-6.48 (m, 4H), 4.05 (qd, J=17.3, 6.1 Hz, 2H), 2.58 (s, 2H), 2.04 (t, J=11.0 Hz, 2H), 1.43 (dd, J=31.0, 10.2 Hz, 4H), 1.10 (t, J=7.2 Hz, 2H).

Example 4

Stability and Photosensitivity of Complex A

The stability of Complex A, i.e. Complex A, in phosphate buffered saline (PBS, pH=7.4) in dark was determined by using RP-HPLC analysis. The HPLC analysis was performed at pre-defined time slots. As shown in FIG. 1a, after incubating the complex at 37° C. for 24 h, 96% percentage of Complex A remained, indicating the complex is stable in the dark. In the presence of 1 mM ascorbate (100 mol equiv.), 89% of Complex A remained after 24 h incubation, indicating that the complex is also stable in the dark even in the presence of a reducing agent.

Figure 1B:
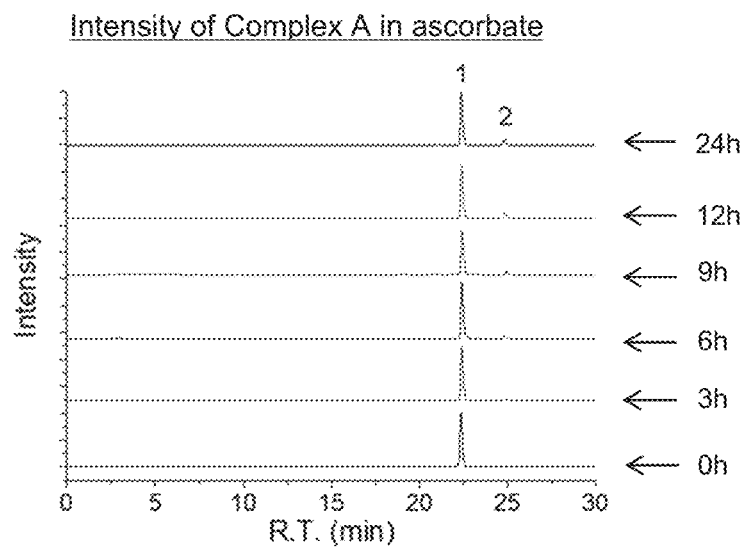
FIG. 1b is a plot showing the intensity of Complex A, i.e. Complex A prepared in an embodiment of the present invention, in 1 mM ascorbate in dark at various time slots (0 h, 3 h, 6 h, 9 h, 12 h, and 24 h), measured by RP-HPLC. Peak 1 corresponds to the intensity of Complex A, and Peak 2 corresponds to the intensity of PPA.
Figure 2:
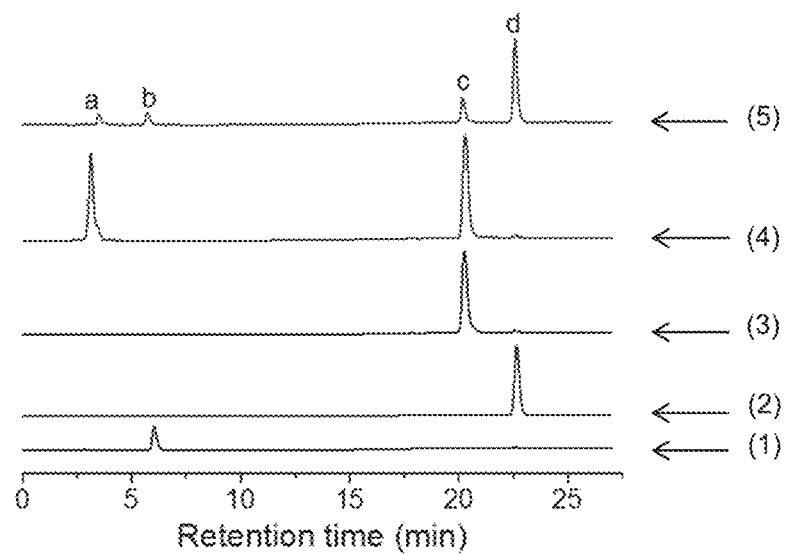
FIG. 2 is a combined RP-HPLC chromatogram showing the retention time of different compounds under various conditions, in which results (1) show the retention time of oxaliplatin in the dark; results (2) show the retention time of PPA in the dark; results (3) show the retention time of Complex A in the dark; results (4) show the retention time of Complex A with equivalent amount of ascorbic acid in PBS buffer (pH 7.4) containing 5% acetonitrile in the dark; results (5) show the retention time of Complex A with equivalent amount of ascorbic acid in PBS buffer (pH 7.4) containing 5% acetonitrile after subjecting to irradiation with a wavelength of 670 nm and a power density of 7 mW/cm$^2$ for 10 min. Peak a corresponds to ascorbic acid, Peak b corresponds to oxaliplatin, Peak c corresponds to Complex A, and Peak d corresponds to PPA.
Figure 3:
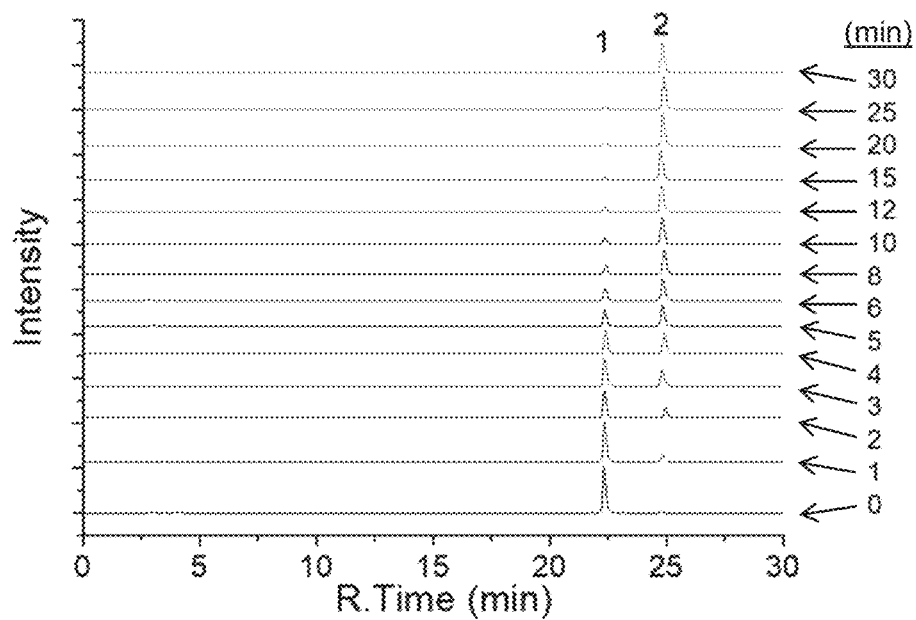
FIG. 3 is a combined RP-HPLC chromatogram showing the intensity of Complex A and PPA after 10 μM Complex A in PBS buffer containing 1% DMF and 1 mM ascorbate was subject to irradiation at 650 nm with a power density of 7 mW/cm$^2$ for different time periods (from 0 min to 30 min). Peak 1 corresponds to Complex A, and Peak 2 corresponds to PPA.
Figure 4:
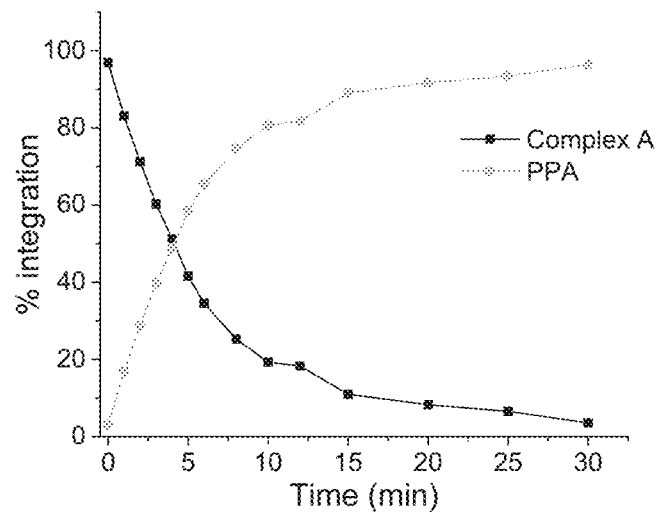
FIG. 4 is a plot showing the amount of Complex A and PPA after subjecting to irradiation at 650 nm calculated from the results in FIG. 3.
Figure 5:
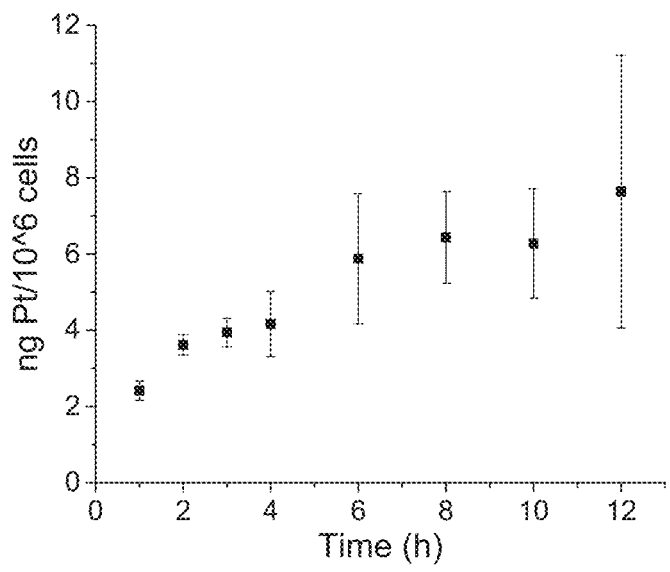
FIG. 5 is a plot showing the accumulation of Complex A in A2780 cells after treatment with 0.5 μM Complex A for 1 to 12 h. It shows the time-dependent accumulation of Complex A in A2780 cells.

The photoactivation property of Complex A was investigated. Buffer solution containing 10 μM Complex A with 1 mM ascorbate in a quartz cuvette was irradiated with LED lamp (650 nm, 7 mW/cm$^2$) under stirring. Samples were analyzed by HPLC. Referring to FIG. 1b, while under irradiation in the presence of ascorbate by red light at 650 nm at a low power density of 7 mW/cm$^2$, the peak of Complex A in the HPLC chromatogram quickly decreased and the peaks of PPA and oxaliplatin increased simultaneously, indicating the reduction of Pt(IV) to Pt(II) along with the dissociation of the axial ligand PPA. After irradiation for 10 min, 81% of Complex A was reduced, and most of the complex was reduced within 30 min. Irradiation of Complex A without the presence of ascorbate also leads to the release of PPA and oxaliplatin, but the reaction speed is much slower.

The inventors further investigated the mechanism of the reduction Complex A. No overlap was observed between the absorbance spectra of PPA and the dihydroxyl Pt(IV) compound [Pt(DACH)(OH)$_2$(ox)]. Therefore, direct energy transfer may not occur between PPA and the Pt(IV) center. In addition, [(Pt(DACH)(OH)$_2$(ox))] cannot be reduced under irradiation in a mixture of the compound and PPA in the presence of ascorbate, indicating that PPA does not serve as a catalyst in the reduction process. The normalized fluorescence intensity of PPA and Complex A is identical, and the fluorescence lifetime of Complex A is 7 ns in DMF, which is the same as PPA. This result suggests that the first excited singlet state of PPA is not involved in the reduction process, excluding the possibility of direct electron transfer from PPA to the Pt(IV) center. Since PPA is able to generate reactive oxygen species (ROS) and singlet oxygen through type I and type II photo process, respectively, the inventors used a hydroxyl radical scavenger, DMSO, and a singlet oxygen scavenger, $NaN_3$, to investigate the electron transfer process. The addition of $NaN_3$ does not alter the photoreduction process significantly, but DMSO is able to promote the reaction as efficiently as ascorbate. Thus, without to be bound by theory, the inventors believe that hydroxy radical is involved in the reaction, and the elimination of hydroxy radical may accelerate the reaction. Furthermore, it was observed that the reduction rate is related to the water content in the system. This result suggests that water is involved in the reaction.

Based on the observation above, the inventors believe that it is hydrogen radical which reduces the Pt(IV) center under irradiation. Complex A can abstract a hydrogen atom from water under irradiation. The electron of the hydrogen atom was then transferred to the Pt(IV) center to yield Pt(III), and the resulted proton was coupled with the axial HO— ligand to generate a dissociated water. This process repeated once to generate the Pt(II) species and the PPA ligand.

Example 5

Cellular Distribution and Cytotoxicity of Complex A

The biological activity of Complex A was subsequently evaluated. A2780 cells were maintained in Roswell Park Memory Institution (RPMI) 1640 medium supported with 10% FBS, 2 mM L-glutamine, and 100 unit/mL penicillin/streptomycin. MCF-7 cells were cultured in Dulbecco's modified Eagle's medium supported with 10% FBS and 100 unit/mL penicillin/streptomycin. MRC-5 cells were maintained in Eagle's minimum essential medium supported with 10% FBS, 1 mM sodium pyruvate, 2 mM L-glutamine, 1 mM non-essential amino acid and 100 unit/mL penicillin/streptomycin. All the cells were incubated in a humidified incubator at 37° C. with 5% $CO_2$ Cytotoxicity test was performed by exposing the cancer cells with Complex A. The viability of cancer cells exposed was evaluated by means of MTT assay. Cells were seeded in 96-well plates at a density of 3,000 cells per well and incubated until the cell confluency reached 50%. Then, the medium was removed and replaced with fresh medium containing different concentrations of complexes with 1% DMF. After 8 h, the medium was aspirated, the well was washed with PBS for twice, and Earle's balanced salt solution (EBSS) was added. The cells were irradiated under 650 nm (7 mW/cm$^2$), or sham irradiated for 30 min. The EBSS was removed, and fresh complete cell culture medium was added to each well. After 40 h, the medium was changed to serum-free medium containing 1 mg/mL MTT. After 2 h additional incubation, the medium was removed, and DMSO (200 μL) was delivered to each well to dissolve the formed purple formazan. The absorbance at 570 nm and 730 nm of each well was measured by using a microplate reader (BioTek PowerWave XS).

The inventors first tested the cellular accumulation of Complex A by ICP-MS. Platinum accumulation in A2780 cells increases dramatically over time before 8 h and very slowly increases over time after 8 h. Thus, an incubation time of 8 h is selected for the following biological assays.

Figure 6:
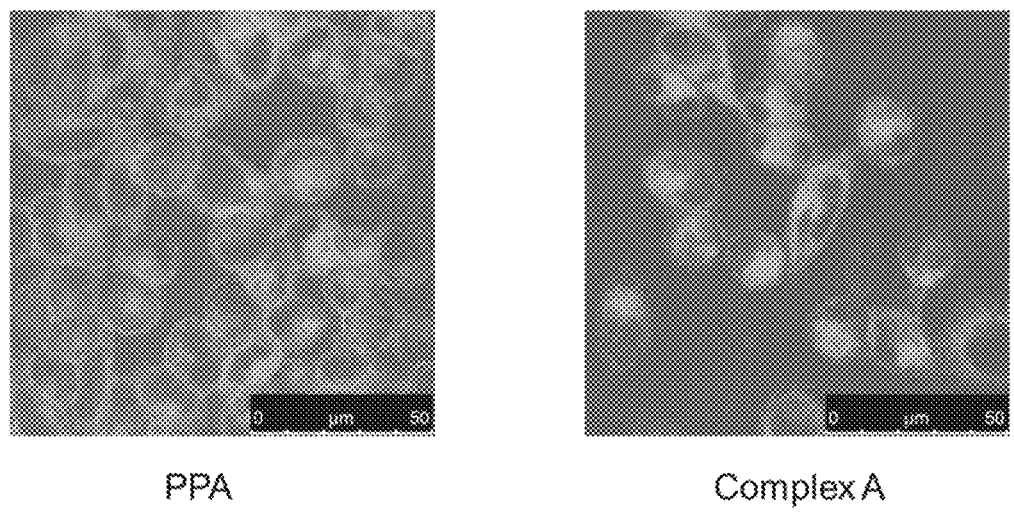
FIG. 6 shows the microscopic images of A2780 cells obtained after treating with Complex A for 8 h in dark. The image on the left demonstrates the cellular distribution of PPA in the treated cells, and the image on the right demonstrates the cellular distribution of Complex A in the treated cells.

The cellular accumulation levels of Pt in A2780 cells treated with Complex A and oxaliplatin after 8 h are 6.4±1.2 and 0.9±0.1 ng Pt/106 cells, respectively. Complex A shows 7.1-fold increased cellular accumulation compared with oxaliplatin, which may due to the increased lipophilicity. The cellular distribution of Complex A was also observed. After treatment at 5 μM for 8 h, most of the compound stays in the cytoplasm, as shown in FIG. 6.

The cytotoxicity of Complex A was then evaluated, using oxaliplatin and PPA as controls. Cells were treated with the compounds for 8 h, followed by irradiation or incubation in the dark, and the cell viability was measured by the MTT assay after 40 h. Complex A is non-toxic to the tested cells in the dark, and is very active under irradiation. The results are shown in Table 1 below.

For example, in A2780 ovarian carcinoma cells, the $IC_{50}$ of Complex A in the dark is higher than 10 μM, while with irradiation, the $IC_{50}$ value is as low as 0.13 μM, which is lower than both PPA and oxaliplatin. Complex A is also active in platinum-resistant A2780 cells. The resistant factors of Complex A and oxaliplatin are 1.5 and 2.7, respectively, and this effect may arise from the combined therapeutic effects of platinum-induced DNA damage and ROS induced oxidative damage by PPA. In addition, Complex A is non-toxic to the tested normal human lung fibroblasts MRC-5 cells in the dark, indicating its lower toxicity to normal cells.

TABLE 1

Cytotoxicity of oxaliplatin, PPA, and Complex A. Cells were treated with complexes for 8 h, followed by irradiation at 650 nm (7 mW/cm²) for 15 min or in the dark. Cell viability was determined by MTT assay at 40 h after irradiation.

| Cell line | Irradiation | $IC_{50}$ (μM) Oxaliplatin | PPA | Complex A |
|---|---|---|---|---|
| A2780 | In the dark | >40 | >10 | >10 |
|  | With irradiation | >40 | 0.34 ± 0.05 | 0.13 ± 0.01 |
| A2780cisR | In the dark | 162 ± 9 | >10 | >10 |
|  | With irradiation | 185 ± 8 | 0.23 ± 0.01 | 0.19 ± 0.01 |
| MCF-7 | In the dark | 110 ± 4.3 | >10 | >10 |
|  | With irradiation | 78.6 ± 8.7 | 0.20 ± 0.02 | 0.044 ± 0.004 |
| MRC-5 | In dark | 122 ± 5.2 | >10 | >10 |

Figure 7:
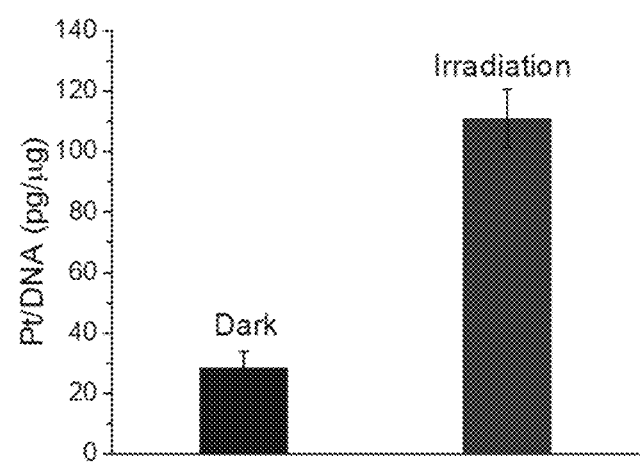
FIG. 7 is a plot showing the level of platinum bound on genomic DNA in A2780 cells treated with 0.5 μM Complex A for 8 h, followed by irradiation at 650 nm with a power density of 7 mW/cm$^2$ for 15 min or in the dark and incubation for 8 h before measurement of platinum.

To further confirm that whether Complex A is reduced to oxaliplatin in cells, the platinum levels in the genomic DNA of cells treated with Complex A were measured. Referring to FIG. 7, only platinum(II) moiety is able to bind genomic DNA efficiently. Under irradiation, the platinum levels on DNA is 110±9.7 pg Pt per μg DNA, and the value is 28±5.5 pg Pt per μg DNA in the dark. This result suggests that Complex A was slowly reduced in cells in the dark, whereas it quickly reduced under irradiation, resulting in DNA binding.

Based on the results in Examples 4 and 5, the inventors found that the complex of the present invention in particular complex of Formula (Vb) undergoes quick reduction to oxaliplatin under the irradiation of red light at 650 nm. In particular, the complex of Formula (Vb) shows low dark-cytotoxicity and is significantly active against human cancer cells including cancer cells having an intrinsic or acquired cisplatin-resistance.

It is thus believed that the complex of the present invention which bears a platinum-based complex in particular an oxaliplatin-based complex preferably at its axial position is effective against cancer as defined herein. The complex of the present invention is suitable to be used as a prodrug as it is found to be stable in the dark even in the presence of ascorbate at physiological concentrations. The stable complex is believed to have minimized side effects originated from non-specific activation of the prodrug by cellular reductants.

Example 6

Stability of Photosensitivity of Complex B

Similar to Example 4, tests were performed to determine the stability and photosensitivity of Complex B prepared in Example 2.

Figure 8A:
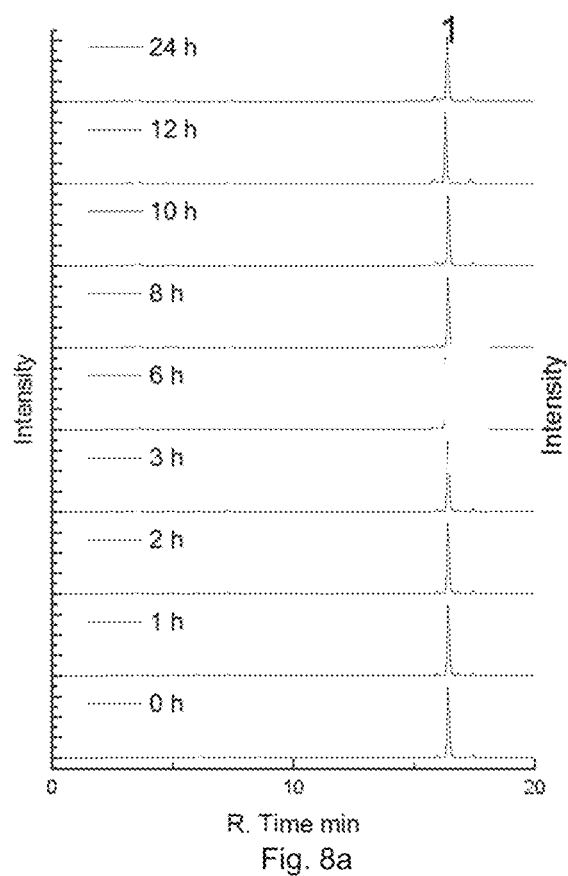
FIG. 8a is a combined RP-HPLC chromatogram showing the intensity of 50 μM Complex B, prepared in an embodiment of the present invention, in the PBS buffer in the dark at different time slots (0 h, 1 h, 2 h, 3 h, 6 h, 8 h, 10 h, 12 h and 24 h), in which Peak 1 corresponds to Complex B and Peak 2 corresponds to Rhodamine B.
Figure 8B:
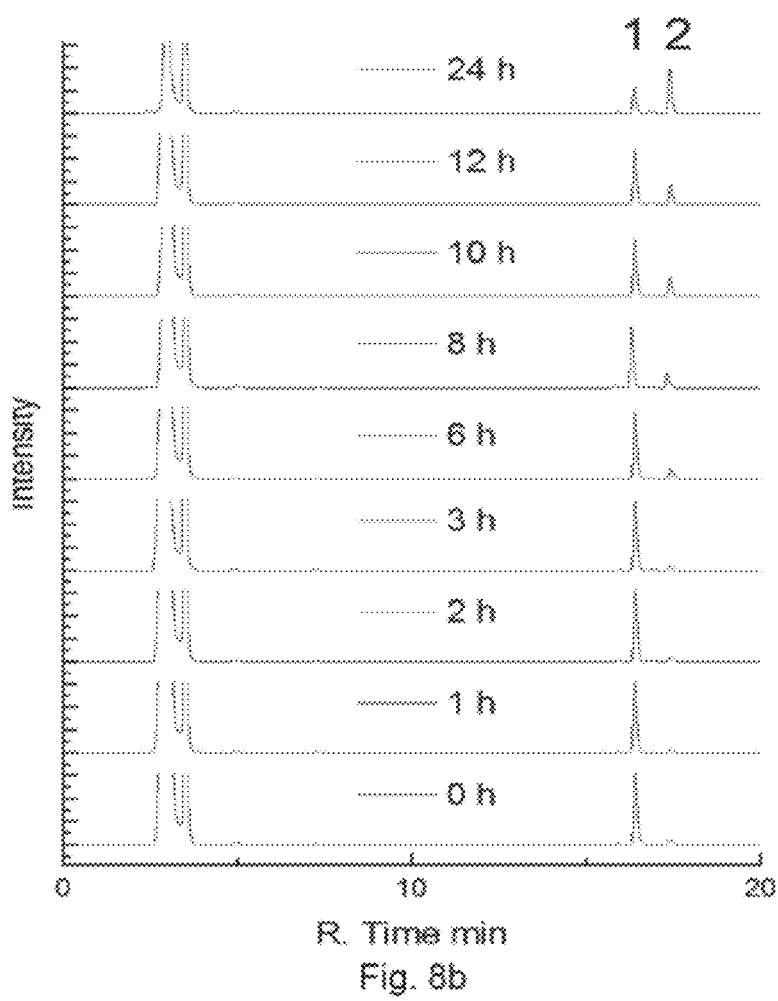
FIG. 8b is a combined RP-HPLC chromatogram showing the intensity of 50 μM Complex B in the PBS buffer with 1 mM ascorbate in the dark at different time slots (0 h, 1 h, 2 h, 3 h, 6 h, 8 h, 10 h, 12 h and 24 h), in which Peak 1 corresponds to Complex B and Peak 2 corresponds to Rhodamine B.

In particular, the PBS buffer (10 mM $Na_2HPO_4$, $KH_2PO_4$, 137 mM NaCl, 2.7 mM KCl, pH=7.4) at the final concentration of 50 μM Complex B with or without ascorbate (1 mM) was incubated in a shaker at 37° C. HPLC analysis was performed at pre-defined time. FIG. 8a shows the intensity of 50 μM Complex B in the PBS buffer in the dark at different time slots (0 h, 1 h, 2 h, 3 h, 6 h, 8 h, 10 h, 12 h and 24 h), in which Peak 1 corresponds to Complex B and Peak 2 corresponds to Rhodamine B. FIG. 8b shows the intensity of 50 μM Complex B in the presence of ascorbate in the dark at different time slots. The results show that Complex B is relative stable in the dark. Complex B is also stable in dark for at least 12 h when a reductant is present.

Then, Complex B was dissolved in PBS buffer (10 mM $Na_2HPO_4$, $KH_2PO_4$, 137 mM NaCl, 2.7 mM KCl, pH=7.4) at the final concentration of 50 μM with or without the presence of 1 mM ascorbate and incubated at 37° C. The solution was irradiated with white light for 2, 5, or 10 min and immediately analyzed by HPLC.

Figure 9A:
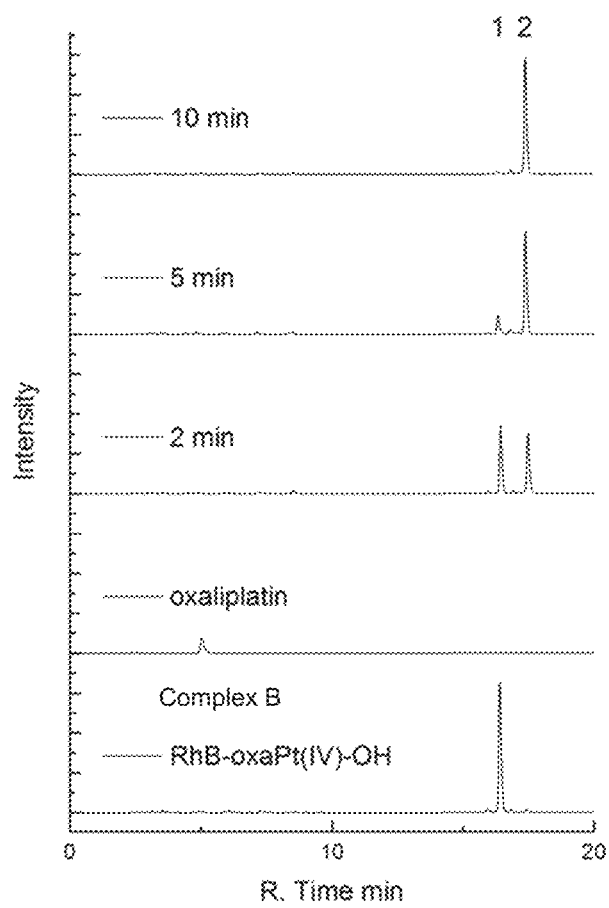
FIG. 9a is a combined RP-HPLC chromatogram showing the intensity of 50 μM Complex B in the PBS buffer after irradiation with white light for 2, 5 or 10 min, in which Peak 1 corresponds to Complex B and Peak 2 corresponds to Rhodamine B.
Figure 9B:
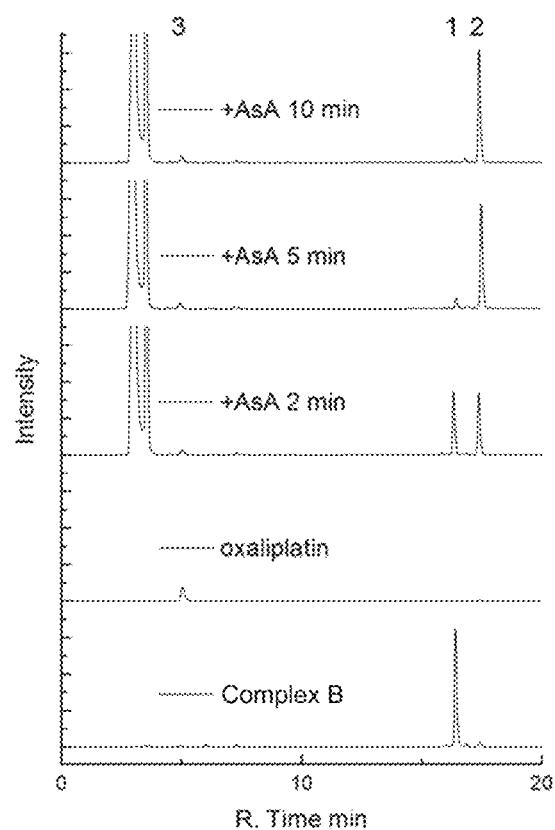
FIG. 9b is a combined RP-HPLC chromatogram showing the intensity of 50 μM Complex B in the PBS buffer with 1 mM ascorbate after irradiation with white light for 2, 5 or 10 min, in which Peak 1 corresponds to Complex B, Peak 2 corresponds to Rhodamine B, and Peak 3 corresponds to oxaliplatin.

Referring to the results in FIGS. 9a and 9b, Complex B is capable of releasing oxaliplatin under irradiation with or without the presence of a reductant. It thus proves that the platinum complex of the present invention bearing an active platinum(IV)-based complex in particular an oxaliplatin-based complex can act as a prodrug and release the active platinum(IV)-based complex in particular an oxaliplatin-based complex at a target area upon irradiation.

The invention claimed is:

1. A platinum complex comprising a structure of Formula (I):

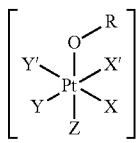

wherein:
  X, X', Y, Y' and Z are independently selected from the group consisting of ammine, hydroxide, halido, oxalate, diamines and —OR, optionally X and X' are linked to form a first bidentate ligand, and Y and Y' are linked to form a second bidentate ligand;
  n is selected from the group consisting of zero, any positive charge, and any negative charge;
  R is a fluorophore moiety having a structure of Formula (III):

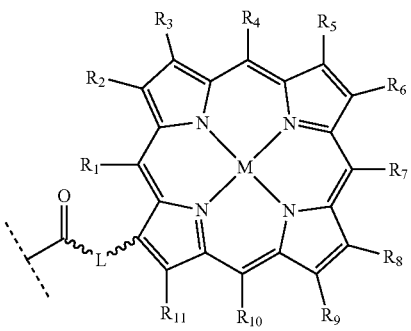

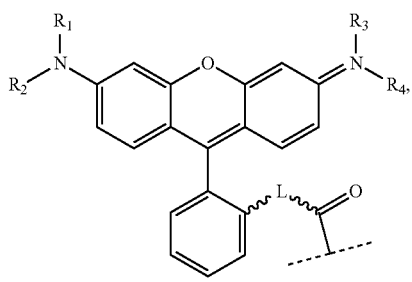

Formula (III)

with L being a linker group, and $R_1$ to $R_4$ each being independently a substituent or a hydrogen atom, wherein an adjacent pair of $R_1$ to $R_4$ may form a fused heterocyclic or carbocyclic ring.

2. The platinum complex of claim 1, wherein
L is —(CH$_2$)$_m$— with m being an integer which is ≥0;
$R_1$ to $R_4$ are independently selected from the group consisting of a hydrogen atom, a hydrocarbon group, a nitrogen-containing group, a heterocyclic group, an oxygen-containing group, a phosphorous-containing group, a sulfur-containing group and a halogen atom.

3. The platinum complex of claim 1, wherein:
L is —(CH$_2$)$_m$— with m being selected from the group consisting of 0, 1, 2, and 3;
$R_1$ to $R_4$ are independently selected from the group consisting of a hydrogen atom, a hydrocarbon group, a nitrogen-containing group, a heterocyclic group, an oxygen-containing group, a phosphorous-containing group, a sulfur-containing group and a halogen atom.

4. The platinum complex of claim 1, wherein Z is not —OR.

5. The platinum complex of claim 3 which comprises a structure of Formula (VI):

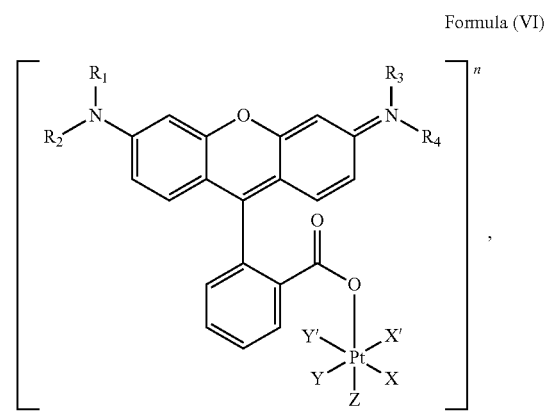

Formula (VI)

wherein X and X' are linked to form a first bidentate ligand, Y and Y' are linked to form a second bidentate ligand, and Z is hydroxido or —OR.

6. The platinum complex of claim 5, wherein X and X' are linked to form oxalato, and Y and Y' are linked to form diamines, and Z is hydroxido.

7. The platinum complex of claim 5, wherein $R_1$, $R_2$, $R_3$ and $R_4$ are independently selected from the group consisting of a hydrogen atom, a saturated or unsaturated C1-C3 alkyl group unsubstituted or substituted with a hydroxy group, and a halogen.

8. The platinum complex of claim 5 which comprises a structure of Formula (VIIa):

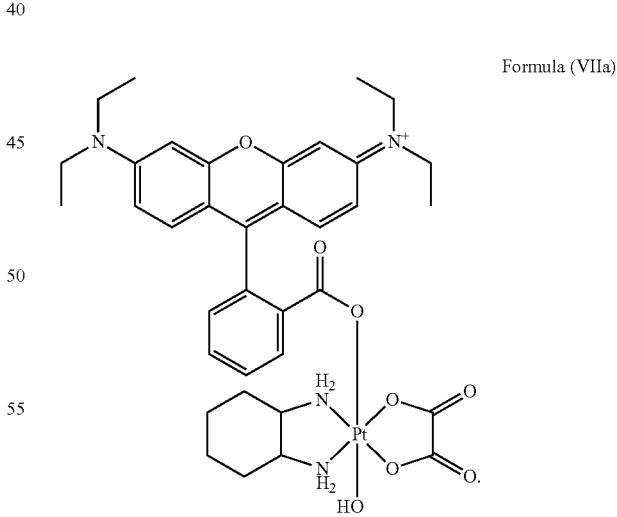

Formula (VIIa)

9. A method for treating a subject suffering from cancer, comprising the step of administering an effective amount of the platinum complex of claim 1 to the subject.

10. The method of claim 9, wherein the platinum complex comprises a structure of Formula (VI):

Formula (VI)

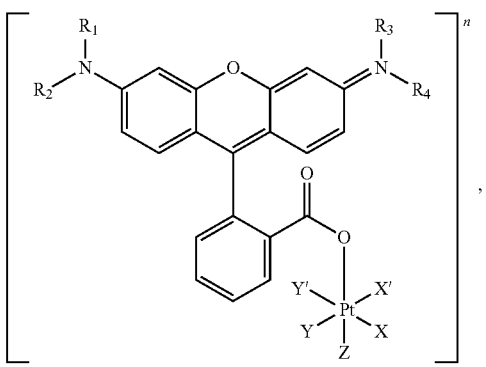

wherein:
X and X' are linked to form a first bidentate ligand, Y and Y' are linked to form a second bidentate ligand, and Z is hydroxido or —OR;
n is selected from the group consisting of zero, any positive charge, and any negative charge; and
$R_1$ to $R_4$ are independently selected from a hydrogen atom, a hydrocarbon group, a nitrogen-containing group, a heterocyclic group, an oxygen-containing group, a phosphorous-containing group, a sulfur-containing group, and a halogen atom.

11. The method of claim 10, wherein $R_1$, $R_2$, $R_3$ and $R_4$ are independently selected from the group consisting of a hydrogen atom, a saturated or unsaturated C1-C3 alkyl group unsubstituted or substituted with a hydroxy group, and a halogen.

12. The method of claim 10, wherein the platinum complex comprises a structure of Formula (VIIa):

Formula (VIIa)

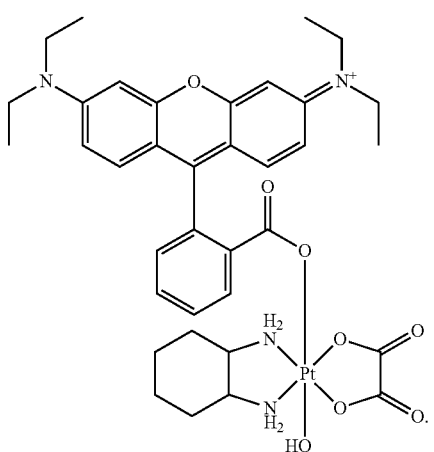

13. The method of claim 9, further comprising the steps of:
locating a target area on the subject for exposure of light with a defined wavelength; and
applying the light to the target area.

14. The method of claim 13, wherein the defined wavelength is within the visible spectrum.

15. The method of claim 9, wherein the defined wavelength is from about 400 nm to 750 nm.

16. The method of claim 9, wherein the cancer has an intrinsic or acquired cisplatin-resistance.

17. The method of claim 9, wherein the cancer is selected from the group consisting of an ovarian cancer, a lung cancer, a breast cancer, and a colorectal cancer.

18. The method of claim 9, wherein the platinum complex is administered in form of a pharmaceutical composition comprising:
(i) the complex; and
(ii) a pharmaceutically tolerable excipient selected from the group consisting of a pharmaceutically tolerable carrier, a salt, a buffer, water, a diluent, a filler, a binder, a disintegrant, a lubricant, a coloring agent, a surfactant, a preservative, and a combination thereof.

19. The method of claim 13, wherein the platinum complex acts as a prodrug.

20. A method for inhibiting the growth of cancer cells comprising the step of contacting a population of cancer cells with an effective amount of platinum complex of claim 1.

21. The method of claim 20, wherein the cancer cells are from one of an ovarian cancer, a lung cancer, a breast cancer, and a colorectal cancer.

22. The method of claim 20, wherein the cancer cells have an intrinsic or acquired cisplatin-resistance.

23. The method of claim 20, wherein the platinum complex comprises a structure of Formula (VI):

Formula (VI)

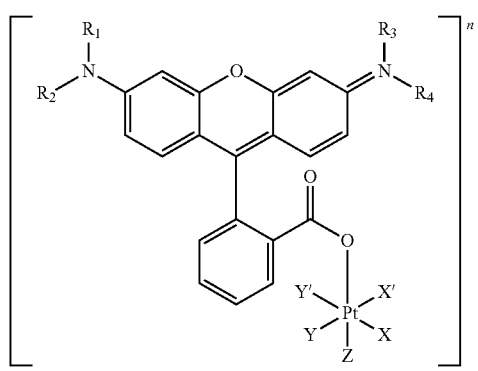

wherein:
X and X' are linked to form a first bidentate ligand, Y and Y' are linked to form a second bidentate ligand, and Z is hydroxido or —OR;
n is selected from the group consisting of zero, any positive charge, and any negative charge; and
$R_1$ to $R_4$ are independently selected from the group consisting of a hydrogen atom, a hydrocarbon group, a nitrogen-containing group, a heterocyclic group, an oxygen-containing group, a phosphorous-containing group, a sulfur-containing group, and a halogen atom.

24. The method of claim 23, wherein $R_1$, $R_2$, $R_3$ and $R_4$ are independently selected from the group consisting of a hydrogen atom, a saturated or unsaturated C1-C3 alkyl group unsubstituted or substituted with a hydroxy group, and a halogen.

25. The method of claim 23, wherein the platinum complex comprises a structure of Formula (VIIa):

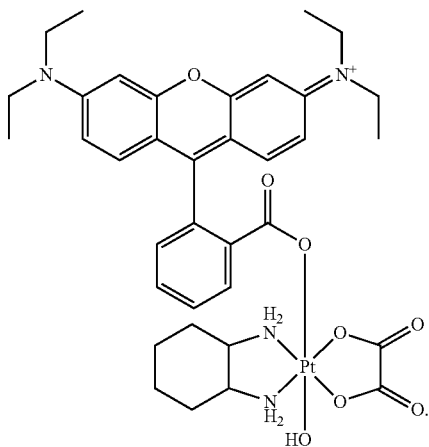

Formula (VIIa)

26. The method of claim 20, further comprising the step of exposing the cancer cells with light having a defined wavelength.

27. The method of claim 20, wherein the defined wavelength is from about 400 nm to 750 nm.

28. A platinum complex comprising a structure of Formula (Va):

Formula (Va)

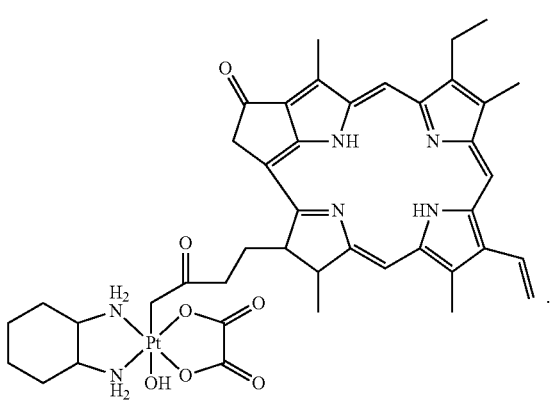

29. A method for treating a subject suffering from cancer, comprising the step of administering an effective amount of a platinum complex to the subject having a structure of Formula (Va):

Formula (Va)

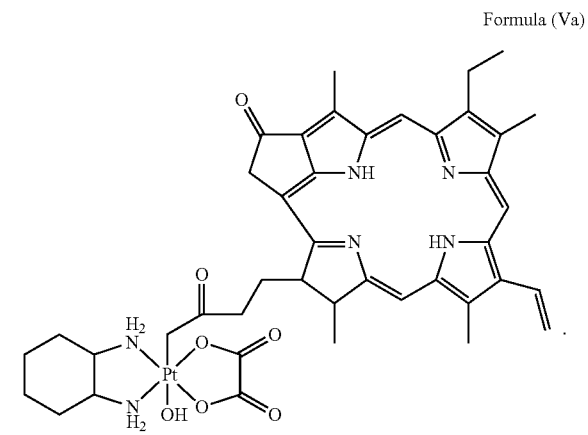

30. The method of claim 29 further comprising the steps of:
   locating a target area on the subject for exposure of light with a defined wavelength; and
   applying the light to the target area.

31. The method of claim 30, wherein the defined wavelength is from about 400 nm to about 750 nm.

32. The method of claim 29, wherein the cancer has an intrinsic or acquired cisplatin-resistance.

33. The method of claim 29, wherein the cancer is selected from the group consisting of ovarian cancer, lung cancer, breast cancer, and colorectal cancer.

34. The method of claim 29, wherein the platinum complex acts as a prodrug.

* * * * *

UNITED STATES PATENT AND TRADEMARK OFFICE
CERTIFICATE OF CORRECTION

PATENT NO. : 10,899,781 B2  
APPLICATION NO. : 15/917966  
DATED : January 26, 2021  
INVENTOR(S) : Guangyu Zhu, Zhigang Wang and Zoufeng Xu Page 1 of 1

It is certified that error appears in the above-identified patent and that said Letters Patent is hereby corrected as shown below:

In the Claims

At Claim 1, Column 35, Lines 21 to 35, the following formula is deleted:

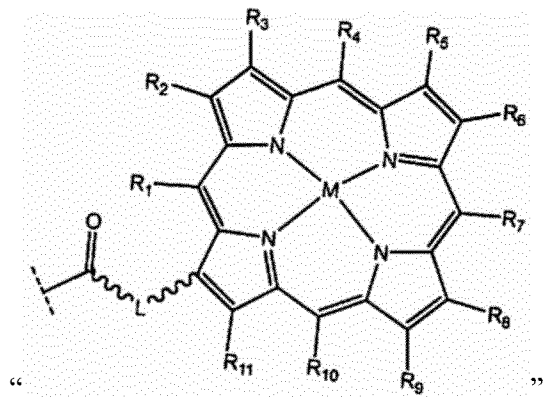

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*